US008623622B2

(12) United States Patent
Srienc et al.

(10) Patent No.: US 8,623,622 B2
(45) Date of Patent: Jan. 7, 2014

(54) GENETICALLY-ENGINEERED ETHANOL-PRODUCING BACTERIA AND METHODS OF USING

(75) Inventors: Friedrich Srienc, Lake Elmo, MN (US); Alan Gilbert, Lebanon, NH (US); Cong Trinh, St. Paul, MN (US); Pornkamol Unrean, Minneapolis, MN (US)

(73) Assignee: Regents of the University of Minnesota, Saint Paul, MN (US)

( * ) Notice: Subject to any disclaimer, the term of this patent is extended or adjusted under 35 U.S.C. 154(b) by 0 days.

(21) Appl. No.: 12/668,982

(22) PCT Filed: Jul. 14, 2008

(86) PCT No.: PCT/US2008/069950
§ 371 (c)(1),
(2), (4) Date: Jun. 23, 2010

(87) PCT Pub. No.: WO2009/012210
PCT Pub. Date: Jan. 22, 2009

(65) Prior Publication Data
US 2010/0255553 A1 Oct. 7, 2010

Related U.S. Application Data

(60) Provisional application No. 60/949,777, filed on Jul. 13, 2007.

(51) Int. Cl.
*C12P 7/06* (2006.01)
*C12P 7/10* (2006.01)
*C12N 9/00* (2006.01)
*C12N 15/00* (2006.01)
*C07H 21/04* (2006.01)

(52) U.S. Cl.
USPC ........ 435/165; 435/161; 435/183; 435/320.1; 536/23.2

(58) Field of Classification Search
None
See application file for complete search history.

(56) References Cited

U.S. PATENT DOCUMENTS 5,000,000 A 3/1991 Ingram et al.

OTHER PUBLICATIONS f Lara et al. Biotechnol Bioeng. Aug. 20, 2006;94(6):1164-75.*
Zhao et al. Appl Microbiol Biotechnol. Mar. 2004;64(1):91-8. Epub Dec. 6, 2003.*
Jackson et al. Microbiology. Feb. 2004;150(Pt 2):407-13.*
Kao et al. J Biol Chem. Oct. 28, 2005;280(43):36079-87. Epub Aug. 31, 2005.*
Maklashina et al. J Biol Chem. Apr. 21, 2006;281(16):11357-65. Epub Feb. 15, 2006.*
Flores et al. J Mol Microbiol Biotechnol. 2004;8(4):209-21.*
Fong et al. J Biol Chem. Mar. 24, 2006;281(12):8024-33. Epub Nov. 30, 2005.*
van der Rest et al. J Bacteriol. Dec. 2000;182(24):6892-9.*
Chica et al. Curr Opin Biotechnol. Aug. 2005;16(4):378-84.*
Sen et al. Appl Biochem Biotechnol. Dec. 2007;143(3):212-23.*
Alper et al., "Engineering yeast transcription machinery for improved ethanol tolerance and production," *Science*, 2006, 314(5805):1565-1568.
Alterthum and Ingram, "Efficient ethanol production from glucose, lactose, and xylose by recombinant *Escherichia coli*," *Appl. Environ. Microbiol.*, 1989, 55(8):1943-1948.
Baba et al., "Construction of *Escherichia coli* K-12 in-frame, single-gene knockout mutants: the Keio collection," *Mol. Syst. Biol.*, 2006, 2:2006.0008.
Bachmann, "Derivations and genotypes of some mutant derivatives of *E. coli* K-12," *E. coli and Salmonella: Cellular and Molecular Biology*, 1996, 2nd Ed., Eds Neidhardt et al., ASM Press, Washington D.C., pp. 2460-2488.
Beall et al., "Parametric studies of ethanol production form xylose and other sugars by recombinant *Escherichia coli*," *Biotechnology and Bioengineering*, 1991, 38(3):296-303.
Bohnsack, "Site-directed mutagenesis using positive antibiotic selection," 1996, *Meth. Mol. Biol.*, 57:1-12.
Carlson and Srienc, "Fundamental *Escherichia coli* biochemical pathways for biomass and energy production: identification of reactions," *Biotech. Bioeng.*, 2004, 85:1-18.
Curran and Carter, "α-Factor Enhancement of Hybrid Formation by Protoplast Fusion in the Yeast *Saccharomyces cerevisiae*," *J. Gen. Microbiol.*, 1983, 129(5):1589-1591.
Curran and Carter, "α-Factor enhancement of hybrid formation by protoplast fusion in *Saccharomyces cerevisiae*," *Curr. Genet.*, 1986, 10(12):943-945.
Datsenko and Wanner, "One-step inactivation of chromosomal genes in *Escherichia coli* K-12 using PCR products," *PNAS*, 2000, 97:6640-6645.
Deng and Nickoloff, "Site-directed mutagenesis of virtually any plasmid by eliminating a unique site," *Anal. Biochem.*, 1992, 200:81-88.
Dien et al., "Fermentation of hexose and pentose sugars using a novel ethanologenic *Escherichia coli* strain," *Enzyme Microb. Technol.*, 1998, 23:366-371.
Farahnak et al., "Construction of Lactose-Assimilating and High-Ethanol-Producing Yeasts by Protoplast Fusion," *Appl. Environ. Microbiol.*, 1986, 51(2):362-367.
Furneisen and Carman, "Enzymological properties of the LPP1-encoded lipid phosphatase from *Saccharomyces cerevisiae*.," *Biochim. Biophys. Acta*, 2000, 1484(1):71-82.
Gilbert et al., "Automated flow cytometry for rapid strain development," Biochemical Engineering XV: Engineering Biology from Biomolecules to Complex Systems, Jul. 15-19, 2007 Quebec City, Canada.

(Continued)

*Primary Examiner* — Christian Fronda
(74) *Attorney, Agent, or Firm* — Fish & Richardson P.C.

(57) ABSTRACT

The present invention describes a number of different microorganisms that have been genetically-engineered to optimize ethanol production. The present invention also describes methods of using such microorganisms to efficiently make ethanol.

28 Claims, 18 Drawing Sheets

(56) References Cited

OTHER PUBLICATIONS

Gilbert et al., "Robust *Saccharomyces cerevisia* strains for ethanol production," Preliminary Program for AIChE 2007 Annual Meeting Salt Lake City, abstract.

Hirayarna et al., "Cloning and characterization of seven cDNAs for hyperosmolarity-responsive (HOR) genes of *Saccharomyces cerevisiae*," *Mol. Gen. Genet.*, 1995, 249:127-138.

Hooks et al., "Lysophosphatidic Acid-induced Mitogenesis Is Regulated by Lipid Phosphate Phosphatases and Is Edg-receptor Independent," *J. Biol. Chem.*, 2001, 276(7):4611-4621.

Ingram and Conway, "Expression of different levels of ethanologenic enzymes from *Zymomonas mobilis* in recombinant strains of *Escherichia coli*," *Applied and Environmental Microbiology*, 1988, 54(2):397-404.

Ingram et al., "Enteric bacterial catalysts for fuel ethanol production," *Biotechnology Progress*, 1999, 15(5):855-866.

Jin et al., "Optimal growth and ethanol production from xylose by recombinant *Saccharomyces cerevisiae* require moderate D-xyulokinase activity," *Applied & Environmental Microbiology*, 2003, 69(1):495-503.

Kacmar et al., "The cytostat: A new way to study cell physiology in a precisely defined environment," *J. Biotechnol.*, 2006, 126(2):163-172.

Keseler et al., "EcoCyc: a comprehensive database resource for *Escherichia coli*," *Nuc. Acids Res.*, 2005, 33:D334-D337.

Kunkel et al., "Rapid and efficient site-specific mutagenesis without phenotypic selection," *Meth. Enzymol.*, 1987, 154:367-382.

Kunkel, "Rapid and efficient site-specific mutagenesis without phenotypic selection," *Proc. Natl. Acad. Sci. USA*, 1985, 82:488-492.

Lewis and Thompson, "Efficient site directed in vitro mutagenesis using ampicillin selection," *Nucl. Acids Res.*, 1990, 18:3439-3443.

Long, et al., "Lipid phosphate phosphatase-1 regulates lysophosphatidic acid- and platelet-derived-growth-factor-induced cell migration," *Biochem J.*, 2006, 394(Pt 2):495-500.

Nissen et al., "Optimization of ethanol production in *S. cerevisiae* by metabolic engineering of the ammonium assimilation," *Metabolic Engineering*, 2000, 2:69-77.

Ochman and Wilson, "Evolutionary history of enteric bacteria," *Escherichia coli and Salmonella typhimurium: cellular and molecular biology*, 1987, Neidhardt et al., editors, Washington, D.C: American Society for Microbiology, pp. 1649-1654.

Ohta et al., "Genetic Improvement of *Escherichia coli* for Ethanol Production: Chromosomal Integration of *Zymomonas mobilis* Genes Encoding Pyruvate Decarboxylase and Alcohol Dehydrogenase II," *Applied and Environmental Microbiology*, Apr. 1991, 57(4):893-900.

Pilquil et al., "Lipid Phosphate Phosphatase-1 Regulates Lysophosphatidate-induced Fibroblast Migration by Controlling Phospholipase D2-dependent Phosphatidate Generation," *J. Biol. Chem.*, 2006, 281(50):38418-38429.

Posfai et al., "Versatile insertion plasmids for targeted genome manipulations in bacteria: isolation, deletion, and rescue of the pathogenicity island LEE of the *Escherichia coli* O157:H7 genome," *J. Bacteriol.*, 1997, 179:4426-4428.

Roca et al., "Metabolic engineering of ammonium assimilation in xylose-fermenting *Saccharomyces cerevisiae* improves ethanol production," *Applied and Environmental Microbiology*, Aug. 2003, 69(8):4732-4736.

Ruiz and Arino, "Function and Regulation of the *Saccharomyces cerevisiae* ENA Sodium ATPase System," *Eukaryotic Cell*, 2007, 6:2175-2183.

Shimada, "PCR-based site-directed mutagenesis," *Meth. Mol. Biol.*, 1996, 57:157-165.

Toke et al., "Isolation and Characterization of the *Saccharomyces cerevisiae* LPP1 Gene Encoding a Mg2+-independent Phosphatidate Phosphatase," *J. Biol. Chem.*, 1998, 273(23):14331-14338.

Trinh and Srienc, "Rational Design of the Most Efficient Utilization of Hexoses and Pentoses by *Escherichia coli*," Preliminary Program for AIChE 2007 Annual Meeting Salt Lake City, abstract, (2007).

Trinh et al., "Design, construction and performance of the most efficient biomass producing *E. coli* bacterium," *Metabolic Eng.*, 2006, 8:628:638.

Von Kamp and Schuster, "Metatool 5.0: fast and flexible elementary modes analysis," *Bioinform.*, 2006, 22(15):1930-1931.

Walfridsson et al., "Ethanolic fermentation of xylose with *Saccharomyces cerevisiae* harboring the *Thermus thermophilus* xylA gene, which expresses an active xylose (glucose) isomerase," *Applied and Environmental Microbiology*, 1996, 62(12):4648-4651.

Zaldivar et al., "Fuel ethanol production from lignocellulose; a challenge for metabolic engineering and process integration," *Appl. Microbiol. Biotechnol.*, 2001, 56:17-34.

Authorized Officer Sun Heup Moon, International Search Report and Written Opinion of the International Searching Authority in PCT/US2008/069950, mailed Feb. 4, 2009, 7 pages.

Authorized Officer Yoshiko Kuwahara, International Preliminary Report on Patentability in PCT/US2008/069950, issued Jan. 19, 2010, 6 pages.

\* cited by examiner

US 8,623,622 B2

GENETICALLY-ENGINEERED ETHANOL-PRODUCING BACTERIA AND METHODS OF USING

CROSS-REFERENCE TO RELATED APPLICATIONS

This application is a National Stage application under 35 U.S.C. §371 and claims benefit of International Application No. PCT/US2008/069950 having an International Filing Date of Jul. 14, 2008, which claims the benefit of priority of U.S. Application No. 60/949,777 having a filing date of Jul. 13, 2007.

TECHNICAL FIELD

This invention relates to microorganisms, and more particularly to microorganisms that produce ethanol and methods of using such microorganisms.

BACKGROUND

It is generally recognized that fossil fuels are limited and that the conventional use of petrochemical resources contributes to environmental effects that impact our global environment. It is clear that a new, sustainable technology that is based on renewable resources has to be developed. One technology that is being as an alternative to petroleum transportation fuels developed is the production of ethanol and other energy carriers from renewable feedstocks such as starch and cellulose.

The hydrolysis of starch or lignocellulosic feedstocks typically result in 6-carbon and 5-carbon sugar precursor mixtures that must be enzymatically converted into ethanol or other valuable energy carriers. The enzymatic conversion can be performed by a number of different microorganisms. Native microorganisms, however, typically have not evolved to carry out desired conversions at the best possible yield. Furthermore, inhibitory substances generated during the hydrolysis steps often negatively affect the microorganisms that are generating ethanol from the sugars.

Thus, efficient and robust microorganisms that are able to function under adverse conditions are needed to establish an optimal and cost efficient sugar-to-ethanol conversion technology. Because different sugar-containing substrates can contain a combination of different sugar precursors, the conditions under which efficient conversion of one sugar-containing substrate into ethanol takes place (e.g., the particular microorganism(s), the particular culture conditions, and the particular inoculum of the microorganism(s)) may be different than those conditions under which efficient conversion of a different sugar-containing substrate into ethanol takes place.

SUMMARY

The present disclosure describes a number of different microorganisms that have been genetically-engineered to optimize ethanol production and further discloses methods of using such microorganisms.

In one aspect, the invention provides a S. cerevisiae yeast having at least a duplication of at least a portion of the lpp1 gene, at least a duplication of at least a portion of the ENA locus, or at least a duplication of at least a portion of both the lpp1 gene and the ENA locus. In some embodiments, the yeast is a haploid strain; in other embodiments, the yeast is a diploid strain. Typically, such yeast convert sugars to ethanol at a yield of at least 95%, and also do not exhibit reduced growth at 20 g/L acetate and at an initial pH of 5.6 or at 50 g/L of ethanol. The yeast described herein exhibit increased resistance to acetate and ethanol compared to wild type yeast and compared to the current industry standard, Ethanol Red™.

In addition, the yeast described herein containing at least a duplication of at least a portion of the lpp1 gene produces less than 0.5 g/L of succinate and less than 7 g/L of glycerol from 300 g/L 6-carbon sugars. Such a yeast produces similar amounts of succinate and glycerol as does the wild type E. coli, but the yeast disclosed herein produces reduced amounts of succinate and glycerol as does the Ethanol Red™ yeast. The yeast described herein containing at least a duplication of at least a portion of the ENA locus exhibits similar properties as does the yeast containing the duplication of at least a portion of the lpp1 gene.

In another aspect, the invention provides an E. coli bacterium that exhibits reduced or undetectable amounts of functional PPP1, OPM4r, ANA2, FEM3, TCA10, FEM2 and FEM7 polypeptides relative to wild type E. coli. Generally, such a bacteria exhibits reduced or undetectable amounts of one or more of the functional polypeptides due to a mutation in a gene encoding the one or more polypeptides or due to deletion of a gene encoding the one or more polypeptides. In one representative embodiment, the bacterial strain has a mutation in each of the zwf, ndh, sfcA/maeB, ldhA, frdA, poxB and pta genes that results in reduced or undetectable amounts of functional PPP1, OPM4r, ANA2, FEM3, TCA10, FEM2 and FEM7 polypeptides, respectively.

Such a bacterial strain can utilize 5-carbon and 6-carbon sugars simultaneously or essentially simultaneously in the production of ethanol, and this C5/C6-utilizing bacteria can produce ethanol at an increased rate compared to wild type E. coli. For example, such a bacterial strain can convert 5-carbon sugars to ethanol at a yield of at least 91%, up to a yield of at least 98% and can convert a mixture of 5-carbon and 6-carbon sugars to ethanol at a yield of at least 85% and up to at least 95%.

The C5/C6-utilizer disclosed herein, under appropriate fermentation conditions, can utilize glycerol as a substrate in the production of ethanol. Representative appropriate fermentation conditions include, without limitation, anaerobic conditions and the presence of an electron acceptor (e.g., nitrate).

In still another aspect, the invention provides an E. coli bacterium that exhibits reduced or undetectable amounts of functional PPP1, OPM4r, ANA2, FEM3, TCA10, FEM2, FEM7, GG1, GLK and MAN1 polypeptides relative to wild type E. coli. As indicated herein, such a bacteria exhibits reduced or undetectable amounts of one or more of the functional polypeptides due to a mutation in a gene encoding the one or more polypeptides or due to deletion of a gene encoding the one or more polypeptides. In one embodiment, this bacterial strain has a mutation in each of the zwf, ndh, sfcA/maeB, ldhA, frdA, poxB, pta, ptsG, glk and manX genes, wherein the mutation results in reduced or undetectable amounts of functional PPP1, OPM4r, ANA2, FEM3, TCA10, FEM2, FEM7, GG1, GLK and MAN1 polypeptides, respectively.

This bacterial strain can utilize 5-carbon sugars exclusively or essentially exclusively in the production of ethanol, and this bacterial strain can produce ethanol at an increased rate compared to wild type E. coli. For example, such a bacterial strain can convert 5-carbon sugars to ethanol at a yield of at least 91% up to at least 99%. Notably, this conversion of 5-carbon sugars to ethanol by this C5-utilizer can be in the presence of 6-carbon sugars.

Either of the bacterial strains described herein further can be disrupted in the mdh gene to result in reduced or undetectable amounts of functional MDH polypeptides. Alternatively, the bacterial strains described herein further can include at least one additional disruption that results in a bacterial strain that exhibits tolerance to higher concentrations of ethanol and/or acetate than is exhibited by the original bacterium or that exhibits a faster rate of growth than is exhibited by the original bacterium.

In yet another aspect, the invention provides methods of making ethanol via the conversion of sugars. Typically, such methods include contacting one or more sugars, under appropriate fermentation conditions, with at least one of the following: the yeast strain disclosed herein, the C5/C6-utilizing bacteria and/or the C5-utilizing bacteria. In one embodiment, the one or more sugars are contacted with a) the C5/C6-utilizing bacteria disclosed herein or the C5-utilizing bacteria disclosed herein and b) the yeast disclosed herein or the C5/C6-utilizing bacteria disclosed herein. For example, the one or more sugars can be contacted with a) and b) sequentially. Such methods also can include collecting the ethanol.

In another aspect, the invention provides for methods of converting lignocellulosic biomass into ethanol. Such methods include hydrolyzing the lignocellulosic biomass to produce a hydrolysate comprising at least one sugar, and contacting at least one sugar from the hydrolysate, under appropriate fermentation conditions, with at least one of the microorganisms described herein.

In still another aspect, the invention provides methods of converting glycerol to ethanol. Such a method can include contacting glycerol with the C5/C6-utilizing bacteria disclosed herein under appropriate fermentation conditions. Such a method also can include collecting the ethanol.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DETAILED DESCRIPTION

Figure 1:
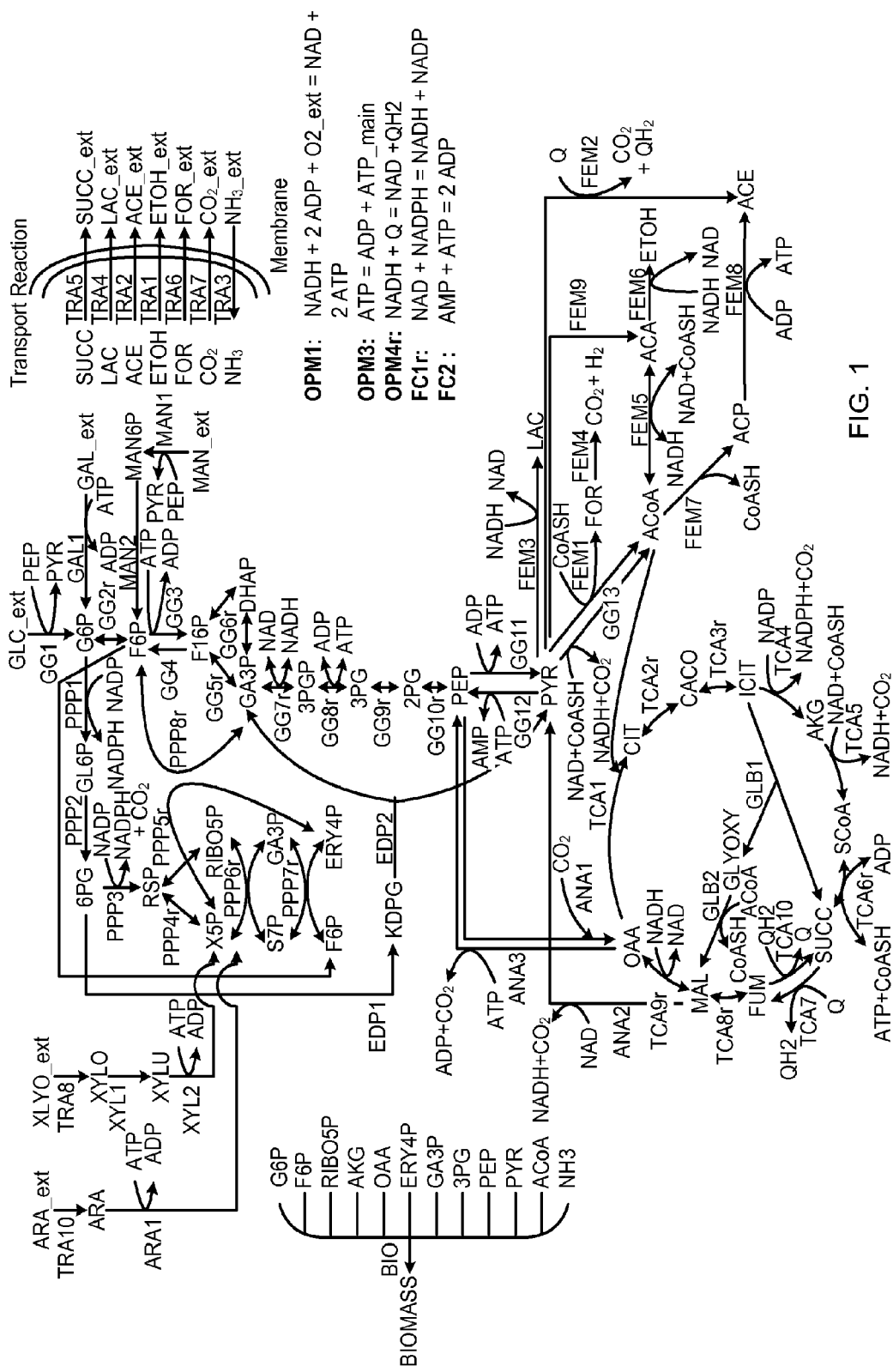
FIG. 1 shows a metabolic map of *E. coli* central metabolism

The present disclosure describes a number of microorganisms that can be used to make ethanol from cellulosic material. Cellulosic material that can be used to make ethanol include, without limitation, hydrolyzed lignocellulosic sources such as feedstock material. The microorganisms disclosed herein exhibit a significant improvement in ethanol yield over wild type strains, and the microorganisms described herein also produce ethanol at a significantly faster rate than do wild type strains.

Microorganisms can produce ethanol from sugars during the fermentation process. The sugars in cellulosic material are predominantly 6-carbon sugars (i.e., hexoses, e.g., glucose, galactose, mannose, gulose, idose, talose, allose, altrose, fructose, sorbose, tagatose, psicose, fucose and rhamnose) and 5-carbon sugars (i.e., pentoses, e.g., arabinose, deoxyribose, lyxose, ribose, ribulose, xylose and xylulose). Generally, wild type microorganisms convert all of the 6-carbon sugars to ethanol first and, due to catabolite repression, only use 5-carbon sugars after 6-carbon sugars have been depleted.

The different microorganisms described herein allow for a mixture of 5-carbon and 6-carbon sugars to be converted into ethanol at a high yield. Using one or more of the microorganisms disclosed herein, different sugar substrates can be converted at different rates to obtain optimal yields of ethanol.

Ethanologenic Yeast Strains

An extremely robust *Saccharomyces cerevisiae* is described herein that contains a duplication of at least a portion of the lipid phosphate phosphatase-1 (lpp1) gene. The *S. cerevisiae* yeast disclosed herein converts 6-carbon sugars to ethanol very efficiently and very rapidly. The lpp1 gene encodes a membrane-associated enzyme that catalyzes a dephosphorylation reaction using several lipid phosphate molecules as substrates. See, for example, Furneisen & Carman, 2000, *Biochim. Biophys. Acta*, 1484(1):71-82; Toke et al., 1998, *J. Biol. Chem.*, 273(23):14331-8; Hooks et al, 2001, *J. Biol. Chem.*, 276(7):4611-21; Long, et al, 2006, *Biochem J.*, 394(Pt 2):495-500; and Pilquil et al, 2006, *J. Biol. Chem.*, 281(50):38418-29.

Another extremely robust *Saccharomyces cerevisiae* is described herein that contains a duplication of at least a portion of the ENA locus. The particular strain disclosed herein contains a duplication of the ENA1, ENA2 and ENA5 genes within the ENA locus, but any combination of the ENA genes at the locus can be duplication. A yeast having a duplication of at least a portion of the ENA locus is able to convert 6-carbon sugars to ethanol very efficiently and very rapidly, and is tolerant to high levels of acetate and ethanol and elevated temperature. The ENA genes encode P-type ATPase sodium pumps (Hirayama et al., 1995, *Mol. Gen. Genet.*, 249:127-38). ENA1, ENA2 and ENA5 previously have been shown to confer salt, pH, and osmolarity tolerance to *S. cerevisiae* (Ruiz & Arino, 2007, *Eukaryotic Cell*, 6:2175-83).

Similar yeast strains can be produced, for example, by genetically-engineering, without limitation, *Kluyveromyces, Pichia*, or oleaginous yeasts such as *Yarrowia* to contain at least a duplication of at least a portion of the lpp1 gene and/or at least a duplication of at least a portion of one or more of the genes at the ENA locus. In addition, a yeast containing at least a duplication of at least a portion of the lpp1 gene can be mated with a yeast that contains at least a duplication of at least a portion of one or more ENA genes. Methods of mating yeast are well known and used routinely in the art.

Yeast containing at least a duplication of at least a portion of the lpp1 gene and/or the ENA gene is able to produce very high yields of ethanol relative to wild type yeast. The conversion of sugars originating from cellulosic feedstock into ethanol can be affected by three characteristics of the microorganism employed: (i) the amount of sugar converted into biomass, (ii) the amount of sugar converted into ethanol, and (iii) the rates at which those conversions take place. The first two characteristics are usually expressed in terms of yield (or ethanol or biomass), which is the ratio of the rate of production of ethanol or biomass to the rate of consumption of the sugar precursor. The overall yield, however, is the ratio of the amount of final product (e.g., ethanol or biomass) obtained in a given time period to the amount of sugar consumed in the same time period.

The kinetics of the reactions are important because biomass production is necessary to provide the catalytic capacity required to carry out the conversion but, once the biomass is formed, it is desirable that all the sugar be converted into ethanol. Ethanol made at the same time that biomass increases is referred to as growth-associated production, while ethanol made when biomass is in a stationary phase is referred to as non-growth-associated production. Therefore, both biomass and ethanol production need to be optimized to get the best ethanologenic strain. Ideally, a strain that exhibits very high, non-growth associated production (rate of ethanol produced per amount of biomass present) is desired, as this strain can convert nearly all the sugars into ethanol very rapidly in the presence of a minimal amount of biomass. A yeast strain as described herein having a duplication of the lpp1 gene and/or the ENA gene can convert sugars to ethanol at a yield of at least 90% (e.g., at least 91%, 92%, 93%, 94%, 95%, 96%, 97%, 98%, or 99%).

In addition, yeast containing at least a duplication of at least a portion of the lpp1 gene and/or the ENA gene exhibits resistance to toxic growth conditions. For example, minimal medium supplemented with 20 g/L acetate (at an initial pH of 5.6) supports a specific growth rate of the yeast disclosed herein that is at least 73% higher (lpp1 duplication) and at least 67% higher (ENA duplication) than in the wild type yeast, and supplemented with 50 g/L ethanol supports a specific growth rate of the yeast disclosed herein that is 172% higher, for both the lpp1 and ENA duplications, than in the wild type yeast. Thus, the ethanol and acetate conditions set forth herein do not reduce or inhibit the growth of a yeast that contains at least a duplication of at least a portion of the lpp1 gene and/or the ENA gene, and the ethanol and acetate resistance exhibited by the yeast disclosed herein exceeds the resistance exhibited by wild type yeast.

Further, yeast that contains at least a duplication of at least a portion of the lpp1 gene and/or the ENA gene produces very little by-products. For example, the yeast disclosed herein having a duplication in the lpp1 gene produce less than 0.5 g/L of succinate and less than 7 g/L of glycerol from starting material containing 300 g/L of 6-carbon sugars. The amount of succinate and glycerol produced by the yeast disclosed herein having a duplication in the lpp1 gene is similar to, but not significantly more than, that produced by wild type yeast. The amount of succinate and glycerol produced by the yeast disclosed herein, however, is less than that produced by Ethanol Red™, a commercially available yeast strain used to convert cellulosic sugars to ethanol. Ethanol Red™, described at fermentis.com/FO/EN/pdf/ethanolredUS.pdf on the World Wide Web, states that fermentation with Ethanol Red™ results in yields of 48 g ethanol per 100 g biomass, and that Ethanol Red™ can continue to grow at ethanol concentrations of up to 18% (v/v) at 35° C.

A duplication of the lpp1 gene or the ENA gene (or at least portions thereof) can be generated using the cytostat technology disclosed herein, or using standard recombinant and molecular biology techniques. Such yeast can be screened for ethanol production as well as ethanol or acetate resistance using methods such as those disclosed herein. Yeast also can be screened using, for example, PCR amplification or Southern blotting, to determine how many copies and which portions of the lpp1 gene and/or the ENA gene are present.

As used herein, wild type yeast refers to a yeast strain designated S288C. S288C is a strain of *S. cerevisiae* that can be obtained from the American Type Culture Collection (ATCC, PO Box 1549, Manassas, Va. 20108) under ATCC No. 204508.

*E. coli* Bacterial Strains

Two different *Escherichia coli* bacterial strains were rationally designed, using elementary mode analysis, to exhibit different sugar-consumption profiles. The bacterial strains described herein consume hexose and pentose sugars, and produce ethanol in the most efficient manner. The two bacterial strains disclosed herein were generated from the ethanol-producing bacterial strain disclosed in Trinh et al. (2006, *Metabolic Eng.*, 8:628:38). The bacterial strain disclosed in Trinh et al. has the following genes disrupted: zwf (encoding a glucose-6-phosphate-1-dehydrogenase (PPP1)), ndh (encoding a NADH dehydrogenase II (OPM4r)), sfcA and maeB (encoding a NAD/NADP-dependent malate enzyme (ANA2)), ldhA (encoding a D-lactate dehydrogenase (FEM3)), and frdA (encoding a fumarate reductase (TCA10)), and produces ethanol at a yield of about 91% on glucose.

The first bacterial strain described herein is able to consume both 5-carbon and 6-carbon sugars simultaneously (or essentially simultaneously) during the process of ethanol production. This bacteria, referred to herein as a C5/C6-utilizer, contains, in addition to the six disrupted genes from the Trinh et al. strain, an additional two genes that have been disrupted, pta and poxB. The C5/C6-utilizing bacteria described herein, in which at least the 8 genes indicated above have been disrupted, exhibits reduced or undetectable amounts of functional PPP1, OPM4r, ANA2, FEM3, TCA10, FEM2 (a pyruvate oxidase encoded by the poxB gene) and FEM7 (a phosphate acetyltransferase encoded by the pta gene) polypeptides. As used herein, "reduced or undetectable amounts of functional polypeptide" refers to a reduction in the amount of polypeptide that has activity relative to wild-type *E. coli*.

The C5/C6-utilizing bacteria described herein can produce ethanol at a much faster rate than can wild type *E. coli*. For example, the C5/C6-utilizing bacteria can convert 5-carbon sugars to ethanol at a yield of at least 91% of the theoretical yield (e.g., at least 92%, 93%, 94%, 95%, 96%, 97%, or 98%), and can convert a mixture of 5-carbon and 6-carbon sugars to ethanol at a yield of at least 85% (e.g., at least 87%, 88%, 89%, 90%, 91%, 92%, 93%, 94%, or 95%). The C5/C6-utilizing bacteria described herein can yield as high as 98% and 95% ethanol on 5-carbon sugars and a mixture of 5-carbon and 6-carbon sugars, respectively.

In addition to being able to utilize 5-carbon and 6-carbon sugars in the production of ethanol, the C5/C6-utilizing bacteria described herein also can utilize glycerol, under appropriate fermentation conditions, to produce ethanol. Glycerol is a by-product of the synthesis of bio-diesel and, therefore, is another abundant source of ethanol given the appropriate microorganism(s). In order to make ethanol from glycerol, the C5/C6-utilizing bacteria described herein must be grown under anaerobic conditions and an electron acceptor must be present in the media. Electron acceptors, include, without limitation, nitrates, nitrites, tetrahydrothiophene 1-oxide, triethylamine N-oxide, and fumarate.

Another *E. coli* bacterium was generated that consumes exclusively, or essentially exclusively, 5-carbon sugars. This bacterium is referred to herein as a C5-utilizer. This C5-utilizing strain, in addition to having the 8 genes indicated above disrupted, also has the following 3 genes disrupted: ptsG, glk and manX. This C5-utilizing bacteria exhibits reduced or undetectable amounts of functional PPP1, OPM4r, ANA2, FEM3, TCA10, FEM2, FEM7, GG1 (a glucose phosphotransferase system encoded by the ptsG gene), GLK (a glucokinase encoded by the glk gene) and MAN1 (mannose phosphotransferase system encoded by the manX gene) polypeptides. In addition to consuming 5-carbon sugars, this C5-utilizing bacteria consumes 5-carbon sugars exclusively or essentially exclusively even in the presence of 6-carbon sugars including glucose.

The C5-utilizing bacteria described herein produces ethanol at an increased rate (e.g., a statistically significantly increased rate) when compared to ethanol production in wild type *E. coli*. The C5-utilizing bacteria disclosed herein is able to convert 5-carbon sugars to ethanol at a yield of at least 91% of the theoretical yield (e.g., at least 92%, 93%, 94%, 95%, 96%, 97%, 98%, or 99%).

The gene disruptions referred to herein include both mutations (e.g., point mutations resulting in conservative and/or non-conservative substitutions, and deletions or insertions or one or more nucleotides) and gene deletions (e.g., knockouts). The bacterial strains described herein (e.g., the 8 genes for the C5/C6-utilizer and the 11 genes for the C5-utilizer) can be disrupted using any of a number of recombinant/molecular techniques including, but not limited to the gene knockouts described in the Examples (e.g., Baba et al., 2006, *Mol. Syst. Biol.*, 2:2006.0008) herein or site-directed mutagenesis as described, for example, in Kunkel, 1985, *Proc. Natl. Acad. Sci. USA*, 82:488; Kunkel et al., 1987, *Meth. Enzymol.*, 154:367; Lewis & Thompson, 1990, *Nucl. Acids Res.*, 18:3439; Bohnsack, 1996, *Meth. Mol. Biol.*, 57:1; Deng & Nickoloff, 1992, *Anal. Biochem.*, 200:81; and Shimada, 1996, *Meth. Mol. Biol.*, 57:157. As indicated above, ethanol production can be optimized when there is a complete or nearly complete absence of functional polypeptides encoded by the indicated genes, although efficient ethanol production can still occur in the presence of reduced amounts (compared to wild type *E. coli*) of each polypeptide. Thus, complete absence of each polypeptide is not required by the present disclosure.

Either a C5/C6-utilizer or a C5-utilizer as described herein can contain one or more additional disrupted genes. For example, a C5/C6-utilizer can be further engineered to disrupt the mdh gene such that the bacteria exhibits reduced or undetectable amounts of functional malate dehydrogenase (MDH) polypeptide. In addition, selective pressure can be placed on a C5/C6-utilizer or a C5-utilizer described herein to generate additional strains or variants having certain characteristics such as, without limitation, tolerance to higher ethanol and/or acetate concentrations or a faster growth rate.

Wild type *E. coli* refers to MG1655. MG1655 is a strain of *E. coli* that that can be obtained from the American Type Culture Collection ATCC #47076. It is further noted that the *E. coli* strains disclosed herein as well as the wild type *E. coli* referred to contain the *Zymomonas mobilis* genes encoding pyruvate decarboxylase (pdc) and alcohol dehydrogenase (adh). These genes are required to obtain ethanol production in *E. coli*. See, for example, Alterthum & Ingram (1989, *Appl. Environ. Microbiol.*, 55(8):1943-8) and U.S. Pat. No. 5,000,000.

Methods of Using Yeast and Bacterial Strains to Produce Ethanol

Among the most promising cellulosic material for making ethanol is feedstock, and one of the most common feedstocks is corn stover, which consists of the stems, cobs, and leaves from the corn plants (i.e., the non-grain material). Currently most corn stover is shredded by mechanical means and incorporated by tillage into topsoil for decomposition. In addition to ligno-cellulosic ethanol production from corn stover, other feedstocks such as sorghum, wheat or another grain can be used. Many grains contain significant cellulose in the pericarp of the kernel and, although 6-carbon sugars are utilized by current strains, the 5-carbon sugars are currently left unconverted and end up as a portion of the by-product. Therefore, conversion of 5-carbon sugars could increase the ethanol yield from this cellulosic source by approximately 10%.

The bacteria and yeast disclosed herein can be used to make ethanol by converting sugars under anaerobic conditions. Generally, sugars are contacted with one or more of the microorganisms disclosed herein (e.g., a yeast strain containing at least a duplication of at least a portion of the lpp1 gene and/or the ENA gene or a C5/C6-utilizing bacteria or a C5-utilizing bacteria) under appropriate fermentation conditions. The sugars can come from a variety of sources including, but not limited to, lignocellulosic biomass. When lignocellulosic material is used in the methods disclosed herein, the material is generally hydrolyzed prior to introducing the microorganism(s). Hydrolysis of cellulosic material can be performed using any number of known methods involving, for example, heat and/or acid treatment.

The particular rate of conversion of sugars into ethanol can be varied according to the particular sugar content and the particular microorganism(s) used. Simply by way of example, a sugar substrate can be contacted first with either of the bacteria described herein (e.g., a C5/C6-utilizing bacteria or a C5-utilizing bacteria) in order to utilize some or most of the 5-carbon sugars first, and then either the yeast described herein or the C5/C6-utilizing bacteria described herein can be added in order to utilize the 6-carbon sugars. As an alternative to adding the first and second microorganism sequentially, two or more microorganisms can be added simultaneously. The particular microorganism selected in the production of ethanol and their introduction into a fermentation culture depends not only on the sugars present but also on the resistance of the microorganism to ethanol and other by-products that may be present in the culture, the inoculum (e.g., the amount of microorganism introduced into the culture), and the growth conditions.

In addition to making ethanol from sugar substrates, an C5/C6-utilizing strain as disclosed herein can make ethanol from glycerol. Importantly, glycerol is a by-product of bio-diesel production, which, using the microorganisms disclosed herein, could be further converted to ethanol.

Following conversion of sugars or glycerol into ethanol, the ethanol can be collected. Ethanol can be collected from a fermentation culture using standard distillation methods.

Articles of Manufacture

An article of manufacture containing any one or more of the microorganisms disclosed herein is provided. An article of manufacture can contain one of the microorganisms disclosed herein (e.g., one or more of the yeast strains, the C5/C6-utilizing bacterial strain, or the C5-utilizing bacterial strain), or an article of manufacture can contain two or more of the microorganisms disclosed herein. For example, an article of manufacture can include a first container having either (or both) the C5/C6-utilizing bacteria or the C5-utilizing bacteria and a second container having either (or both) a yeast containing at least a duplication of at least a portion of the lpp1 gene and/or the ENA gene or the C5/C6-utilizing bacteria. Articles of manufacture disclosed herein also can include, for example, components necessary for growth of the particular microorganism(s).

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the invention described in the claims.

EXAMPLES

Section A. Bacteria Production

Example 1

Medium

All controlled-batch bioreactors for bioethanol production used Lauria Bertani (LB) rich medium containing 5 g/L NaCl, 5 g/L yeast extract, 10 g/L trypone, 80 g/L of total sugars (unless otherwise specified), and 10 μg/mL tetracycline. LB components were autoclaved. Sugars and tetracycline were sterile filtered and added into bioreactors. Growth experiments conducted in baffled shake flasks used defined medium containing 12.8 g/L $Na_2HPO_4*7H_2O$, 3 g/L $KH_2PO_4$, 0.5 g/L NaCl, 1 g/L $NH_4Cl$, 0.2% (v/v) 1 M $MgSO_4$, 0.01 g/L $CaCl_2$, 0.1% (v/v) stock trace metals solution, 1 mg/L thiamine, and 4 g/L total sugars (unless otherwise specified). The stock trace metal solutions consisted of 0.15 g/L $H_3BO_4$, 0.065 g/L $CoSO_4$, 0.05 g/L $ZnSO_4*7H_2O$, 0.015 g/L $MnCl_2*4H_2O$, 0.015 g/L $NaMo_4*2H_2O$, 0.01 g/L $NiCl_2*6H_2O$, 0.005 g/L $CuSO_4*5H_2O$, and 3 g/L $Fe(NH_4)$ citrate.

Example 2

Growth in Batch Bioreactors

Batch bioreactor experiments were conducted in 10 L Braun bioreactors (Biostat MD, B. Braun Biotech International, Melsungen, Germany) with a working volume of 6 L under anaerobic conditions. The temperature and agitation rate were set at 37° C. and 200 rpm, respectively. Single colonies were picked from freshly streaked plates and grown overnight in 15 mL tubes containing 5 mL of rich medium. The cultures were then transferred to 250 mL capped shake flasks containing 100 mL of rich medium and grown exponentially at 37° C. and 225 rpm. Those cultures were then used to inoculate the bioreactor.

The medium used in the inoculation cultures and in the bioreactors was identical. The initial optical density measured at 600 nm wavelength ($OD_{600\ nm}$) after inoculation in all batch bioreactors was 0.05. To maintain anaerobic growth conditions, nitrogen was sparged into bioreactors through a 0.2 µm filter at a volumetric flow rate of 100 mL/min at least 4 hours before inoculation and throughout the fermentation. The exhaust gas was first passed through an exhaust gas condenser, then a 0.2 µm filter, a pressure regulator, and finally into the prima δ-B mass spectrometer (ThermoOnix, Houston, Tex.) to analyze gas composition. The reactor gauge pressure was set at 1 psig to minimize air diffusion into bioreactors so as to maintain anaerobic growth conditions. pH was controlled at 6.5 using 6M NaOH and 40% $H_3PO_4$. The anaerobic growth conditions could be confirmed by negative detection of oxygen signals from the mass spectroscopy. The fermentation was completed when $H_3PO_4$ starts accumulating in bioreactors.

Example 3

Analytical Techniques

Optical density of a culture was measured at a wavelength of 600 nm in 1 cm cuvettes using a Hewlett Packard 8452A Diode Array spectrophotometer (Palo Alto, Calif.). 10 ml of culture was withdrawn periodically from a bioreactor and immediately processed to determine cell dry weight and secreted metabolites in supernatant. First, the sample was spun at 3500×g and 4° C. for 25 min. Then its supernatant was stored at −20° C. for later analysis, and the cell pellet was washed once with deionized water, vacuum filtered, and weighed in a weighing dish after being dried in the 65° C. oven for at least one day. The weight conversion of optical density is 1 $OD_{600\ nm}$=0.259 g/L ($R^2$=0.942). Metabolite concentrations were determined using a HPLC system (Shimadz10A, Shimadzu, Columbia, Md.) equipped with an autosampler (SIL-10AF), a cation exchange column (HPX-87H, Biorad Labs, Hercules, Calif.) and two detectors in series including a UV-VIS detector (SPD-10A) and a refractive index detector (RID-10A). Samples from cell supernatants were first filtered through a 0.22 µm filter unit. Then 10 µl of samples were loaded into the column operated at 65° C. A 5 mM $H_2SO_4$ solution was used as the mobile phase and run isocratically at a flow rate of 0.5 mL/min.

Example 4

Bacterial Strains and Plasmids

Table 1 shows a list of bacterial strains and plasmids used in this study. *E. coli* MG1655 was used as the wild type. All mutants with single deleted genes were obtained from the single gene knockout library, the Keio collection (Baba et al., 2006, *Mol. Syst. Biol.*, 2:2006.0008). The mutants were derived from BW25113, a derivative of MG1655 and constructed using the technique of one-step disruption of chromosomal genes (Datsenko & Wanner, 2000, *PNAS*, 97:6640-5). To construct mutants with multiple deleted genes, all single deleted genes whose parent strains are BW25113 were first transferred into the wild type by generalized P1 transduction. Then, mutants with multiple deleted genes were created by multiple steps of P1 transduction from strains with a single deleted gene {Trinh et al., 2006, *Metab. Eng.*, 8:628-38}. At each step, the recipient strain that contained one or more deleted genes had its kanamycin cassette removed by using the temperature-sensitive helper plasmid, pFT-A (Posfai et al., 1997, *J. Bacteriol.*, 179:4426-8). Donor strains used to prepare P1 lysate had a single deleted gene with intact kanamycin cassette. PCR amplification reactions were used with the primers shown in Table 2 to confirm gene disruption.

TABLE 1

List of strains and plasmids

| Strains | Genotypes | Sources |
|---|---|---|
| MG1655 | Wild type | * |
| JW0855 | BW25113, poxB::kan$^+$ | (Baba et al., 2006, supra) |
| JW2294 | BW25113, pta::kan$^+$ | (Baba et al., 2006, supra) |
| JW1087 | BW25113, ptsG::kan$^+$ | (Baba et al., 2006, supra) |
| JW2385 | BW25113, glk::kan$^+$ | (Baba et al., 2006, supra) |
| JW1806 | BW25113, manX::kan$^+$ | (Baba et al., 2006, supra) |
| TCS062 | MG1655, Δzwf Δndh ΔsfcA ΔmaeB ΔldhA ΔfrdA::kan$^-$ | Trinh et al., 2006, supra |
| TCS083 | MG1655, Δzwf Δndh ΔsfcA ΔmaeB ΔldhA ΔfrdA ΔpoxB Δpta::kan$^-$ | present study |
| CT1101 | MG1655, Δzwf Δndh ΔsfcA ΔmaeB ΔldhA ΔfrdA ΔpoxB Δpta ΔptsG Δglk ΔmanX::kan$^-$ | present study |
| Plasmids | | |
| pFT-A | amp$^R$ | (Posfai et al., 1997, supra) |
| pLOI297 | pUC18 backbone vector containing pdc$_{ZM}$ and adhE$_{ZM}$ from *Zymomonas mobilis* under lac promoter with amp$^R$ and tet$^R$ | ATCC68239 |

*Bachmann, 1996, "Derivations and genotypes of some mutant derivatives of *E. coli* K-12," In *E. coli* and *Salmonella*: Cellular and Molecular Biology, 2nd Ed., Eds Neidhardt et al., ASM Press, Washington D.C., pp. 2460-88.

TABLE 2

Primers

| Tested genes | Outside primers | SEQ ID NO: |
|---|---|---|
| zwf | 5'-CGC GTA ACA ATT GTG G-3' | 1 |
|  | 5'-CTG GAT TTT TTC CAG C-3' | 2 |
| ndh | 5'-GCG TTC AAA ACC CTC GGG-3' | 3 |
|  | 5'-GAC ACC AAT CCC GAT ACC CGC C-3' | 4 |

TABLE 2-continued

Primers

| Tested genes | Outside primers | SEQ ID NO: |
|---|---|---|
| maeA | 5'-CGG ATG ATG TTC TGC ATA GCA GGT G-3' | 5 |
|  | 5'-CCC AAC CGG CAG AAA ACG CCC CGC T-3' | 6 |
| maeB | 5'-CTG TTT GAT GCC GTC TAA CTC GTT C-3' | 7 |
|  | 5'-CTT TAT CCA TGA GTC GCC GCC TGT G-3' | 8 |
| frdA | 5'-CGG TAA TTA ATA AGG CGC AGA GCG-3' | 9 |
|  | 5'-CTC CAG TTT TTG ACA AGG GC-3' | 10 |
| ldhA | 5'-CGC AAC AAA CGC GGC TAC-3' | 11 |
|  | 5'-CGG CTT TAT ATT TAC CCA GC-3' | 12 |
| pta | 5'-CTG CCG CTA TGT TGA AGA CA-3' | 13 |
|  | 5'-GTT CGC CTG CTT CGT TAG TC-3' | 14 |
| poxB | 5'-ATG GAT ATC GTC GGG TTT GA-3' | 15 |
|  | 5'-AAG CAA TAA CGT TCC GGT TG-3' | 16 |
| ptsG | 5'-GGA TCG GTT ACT GGT GGA AA-3' | 17 |
|  | 5'-GAC CAC CAC GTT AGC CAT CT-3' | 18 |
| glk | 5'-CAG GCA CAT AAG GCA ATC AG-3' | 19 |
|  | 5'-TAT TCC TTA TGC GGG GTC AG-3' | 20 |
| manX | 5'-GCA AAC GAA TGT GAC AAG GA-3' | 21 |
|  | 5'-CGG TTT TCA TAT CCC CAA GA-3' | 22 |

Example 5

Ethanol Yield Calculations

Ethanol yields on sugars were determined by $$Y_{ETOH/Glc} = \frac{r_{ETOH}}{r_{Glc}}$$

(g ethanol/g sugars). The $r_{ETOH}$ (g ethanol/L/hr) and $r_{Glc}$ (g glucose/L/hr) values represent the ethanol production rate and glucose consumption rate, respectively. In all experiments, $Y_{ETOH/Glc}$ appeared to be relatively constant since the linear repression of ethanol produced (g/L) and glucose consumed (g/L) yielded a perfect fitting with $R^2 > 0.99$. It is noted that percent yield often refers to percent of theoretical yield.

E. coli Metabolic Network

The metabolic network was constructed for E. coli that can grow on pentoses and hexoses including D(+)-xylose, L(+)-arabinose, D(+)-glucose, D(+)-galactose, and D(+)-mannose by using available public database (e.g., Keseler et al., 2005, Nuc. Acids Res., 33:D334-7) and published references (e.g., Neidhardt, 1987, Amer. Soc. Microbio., 1654:xlvii p; and Carlson & Srienc, 2004, Biotech. Bioeng., 85:1-18). FIG. 1 shows the metabolic network.

The constructed model represents the core of intermediary metabolism of E. coli. The model includes 68 reactions, 49 of which are irreversible, and 67 metabolites, 51 of which are internal. The model also considers the pyruvate decarboxylase reaction (FEM9), which converts pyruvate to acetaldehyde. The pyruvate decarboxylase reaction does not exist in E. coli, but is introduced into E. coli via the plasmid pLOI297 (see, for example, U.S. Pat. No. 5,000,000). Some reactions in sugar degradation pathways that occur in series without branches are shown together in FIG. 1 to simplify the model without affecting the analysis. All elementary modes of the E. coli metabolic network were calculated using METATOOL 5.0, the current fast and flexible Matlab-based software to handle complex metabolic network (von Kamp & Schuster, 2006, Bioinform., 22(15):1930-1).

Example 6

Design of an Efficient Ethanologenic E. coli Strain

It is desirable to design an efficient ethanologenic E. coli strain that can efficiently convert pentoses and hexoses to ethanol under anaerobic conditions at a theoretical yield of 0.51 g ethanol/g sugars. Since elementary mode analysis can identify all possible pathways inherent to a metabolic network, optimal pathways can be selected to meet the design criteria for an efficient ethanologenic E. coli strain and to engineer such strains.

Example 7

Identification of Efficient Pathways for Pentose Utilization

First, efficient pathways for utilizing xylose and arabinose were identified because xylose and arabinose are the dominant 5-carbon sugars found in biomass. Since both arabinose and xylose are transported into E. coli cells by ABC transporters and phosphorylated to xylose-5-phosphate by their corresponding kinase enzymes, the total number of elementary modes for growth on arabinose and xylose was the same. That is, 8,150 elementary modes (EMs) were identified that can be used by E. coli to metabolize either xylose or arabinose under aerobic or anaerobic conditions. Among these 8,150 EMs, 2,054 EMs could consume either xylose or arabinose under anaerobic conditions. Of those 2,054 anaerobic EMs, there were 1,952 EMs that could make ethanol with or without synthesizing biomass, 777 EMs that could synthesize biomass with or without making ethanol, and 707 EMs that could co-produce ethanol and biomass (Table 3). The set of EMs that are not involved in biomass production are associated with cell maintenance and/or production of by-products only. These EMs represent a production phase in E. coli when one of the non-carbon substrates required for growth is depleted.

Figure 2:
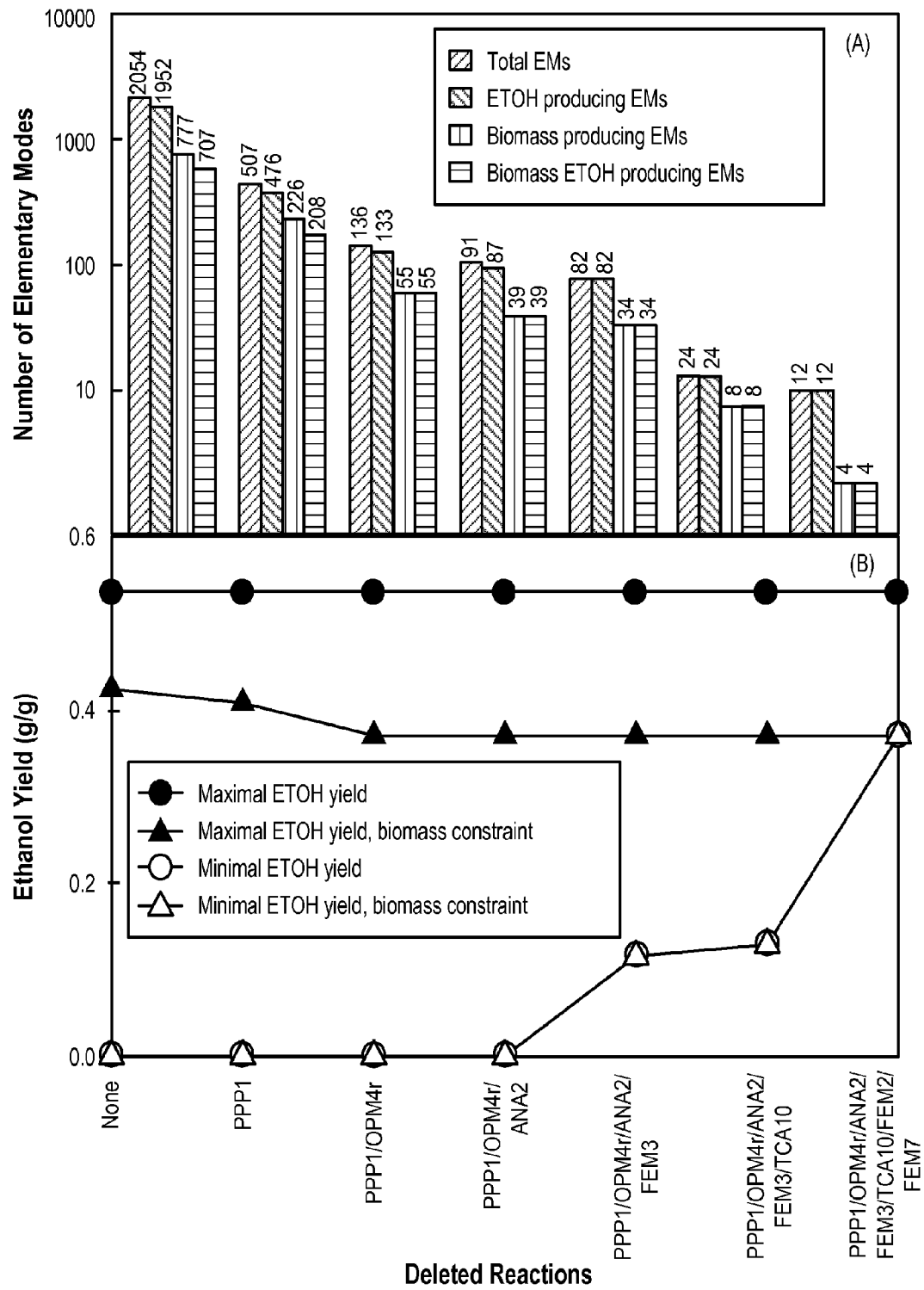
FIG. 2 shows graphs that demonstrate the identification of multiple deleted reactions for the most efficient ethanologenic *E. coli* strain utilizing xylose or arabinose under anaerobic conditions. Panel (A) shows the effect of multiple deleted reactions on the number of elementary modes. Panel (B) shows the effect of multiple deleted reactions on the range of minimal and maximal ethanol yields with and without a constraint of biomass synthesis.

Under anaerobic conditions, 1,952 EMs made ethanol with or without co-production of biomass and achieved a yield range of approximately 0.00-0.51 g ethanol/g sugars (FIG. 2). The lower ranges of ethanol yield were likely due to pathways competing for the use of carbon sources to make biomass and/or other by-products. The maximal yield of ethanol occurs during the ethanol production phase. Under given growth conditions, a wild type E. coli can use a combination of any EM among the complete set of 2,054 anaerobic EMs (not necessarily the subset of ethanol producing EMs) to maximize its fitness. Therefore, a wild type E. coli may not necessarily be an efficient ethanologenic strain for high ethanol production.

To develop an efficient ethanologenic E. coli, a wild type E. coli was rationally engineered to operate only under the optimal ethanol-producing pathways. This rational approach required deletion of multiple reactions, which reduced a large portion of undesirable EMs that result in production of by-products, while leaving EMs that can still support growth and achieve an upper range of ethanol yield. As demonstrated in FIG. 2, deletion of the following set of 7 reactions including PPP1, OPM4r, ANA2, FEM3, TCA10, FEM2, and FEM7 reduced the total number of anaerobic EMs from 2,054 to 12, the set of ethanol-producing EMs from 1,952 to 12, the set of biomass-producing EMs from 777 to 4, and the set of EMs that produce both biomass and ethanol from 707 to 4. Deletion of these reactions caused the range of ethanol yields to narrow and, therefore, yields approached the upper limit (0.36 to 0.51 g ethanol/g sugars). More importantly, deletion of these reactions left only the most efficient ethanol producing pathways because the total number of EMs and the number of ethanol producing EMs were the same (i.e., both were 12). In addition, the ethanol production must be coupled with biomass synthesis during the growth phase because, upon deletion of these reactions, the number of biomass-producing EMs and the number of EMs that made both biomass and ethanol were the same (i.e., both were 4 EMs). The remaining 8 EMs were involved only in making ethanol with or without the production of ATP.

TABLE 3

Summary of elementary modes that utilize different sugars as carbon sources

| | carbon sources | | | | |
|---|---|---|---|---|---|
| | xylose or arabinose | glucose | mannose | galactose | xylose and glucose |
| All EMs | 8,150 | 18,415 | 13,405 | 20,985 | 45,926 |
| Total anaerobic EMs | 2,054 | 5,010 | 2,841 | 3,636 | 12,633 |
| ETOH-producing anaerobic EMs | 1,952 | 4,913 | 2,745 | 3,519 | 12,154 |
| Biomass-producing anaerobic EMs | 777 | 4,157 | 2,134 | 2,876 | 9,442 |
| Biomass- and ETOH-producing anaerobic EMs | 707 | 4,080 | 2,064 | 2,785 | 9,022 |

Example 8

Identification of Efficient Pathways for Hexose Utilization

Elementary mode analysis was used to identify the most efficient pathways that *E. coli* uses to convert three abundant hexoses typically found in biomass including glucose, mannose and galactose into ethanol. Upon entering the cytosol, both glucose and mannose are phosphorylated by the phosphoenolpyruvate transferase system (PTS). However, galactose is phosphorylated inside the cytosol by galactose kinase. Differences in degradation pathways of individual hexoses resulted in a different total number of elementary modes that *E. coli* can utilize (Table 3). Individual utilization of galactose had 20,985 EMs, which was the largest number of EMs for the 6-carbon sugars. Under anaerobic conditions, however, glucose utilization had the largest number of EMs (5,010 EMs).

Figure 3:
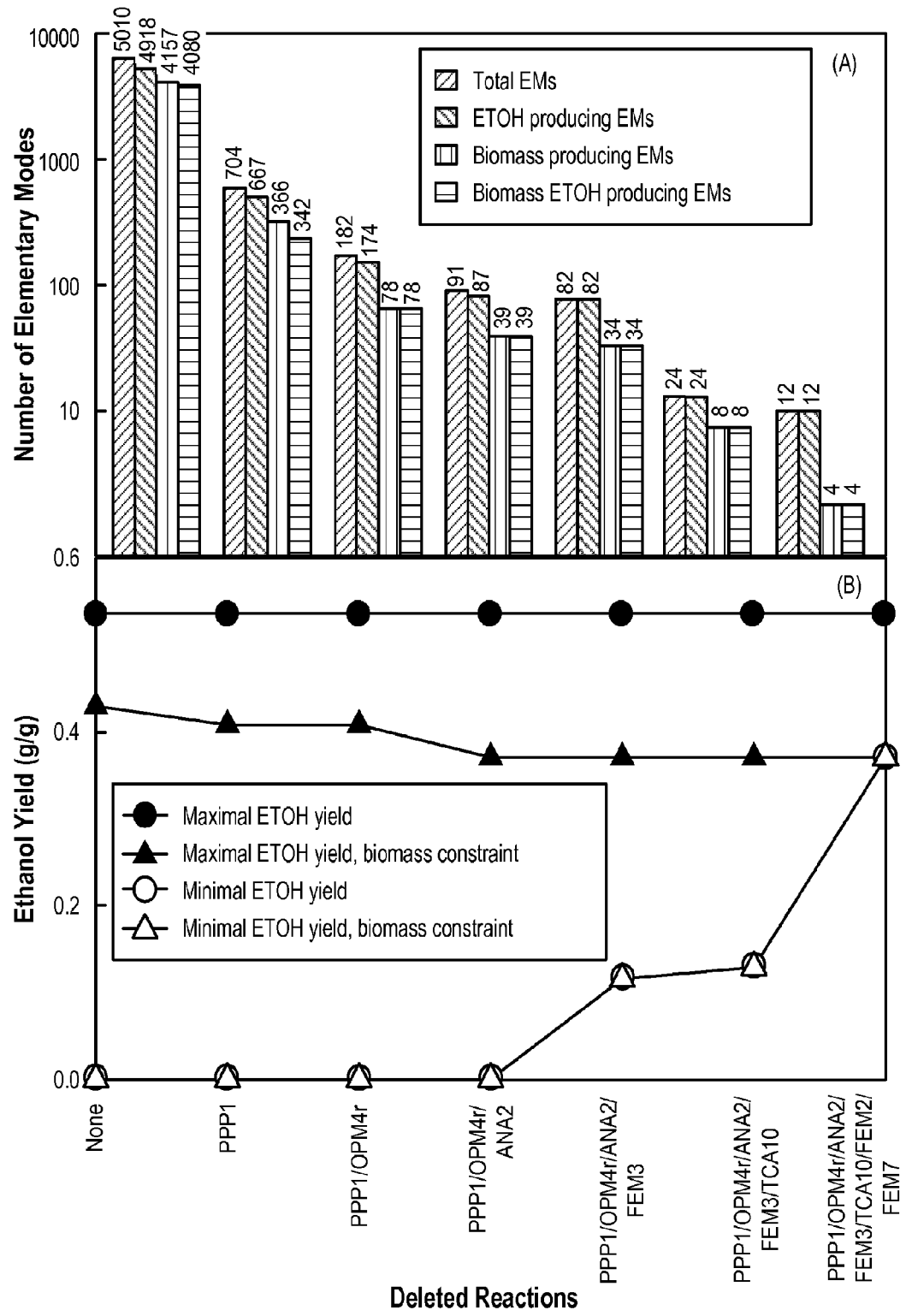
FIG. 3 shows graphs that demonstrate the identification of multiple deleted reactions for the most efficient ethanologenic *E. coli* strain utilizing glucose under anaerobic conditions. Panel (A) shows the effect of multiple deleted reactions on the number of elementary modes. Panel (B) shows the effect of multiple deleted reactions on the range of minimal and maximal ethanol yields with and without a constraint of biomass synthesis.

The same strategy described above for pentoses was used to identify multiple deleted reactions that result in the most efficient ethanol producing pathways. FIG. 3 demonstrates the effect of multiple deleted reactions on restricting the total number of EMs to only the efficient ethanol-producing EMs that can achieve high ethanol yields from glucose. Deletion of the same following set of 7 reactions including PPP1, OPM4r, ANA2, FEM3, TCA10, FEM2, and FEM7 reduced the total number of anaerobic EMs from 5,010 to 12, the set of ethanol producing EMs from 4,913 to 12, the set of biomass producing EMs from 4,157 to 4, and the set of EMs that produce both biomass and ethanol from 4,084 to 4. Similar to the results obtained in the presence of pentose, the range of ethanol yields in the presence of glucose became narrow and approached the upper limit (0.36 to 0.51 g ethanol/g sugars). Similar results also were obtained for growth on galactose and mannose. The total number of anaerobic EMs and the set of ethanol-producing EMs were reduced to 12. The set of ethanol-producing EMs and the set of EMs that produce biomass and ethanol were reduced to 4. Interestingly, the total number of anaerobic EMs, the set of ethanol producing EMs, the set of biomass producing EMs, and the set of EMs that produce both biomass and ethanol became the same for growth on glucose or xylose (arabinose) in the absence of PPP1, OPM4r, and ANA2. For growth on galactose, mannose, or xylose (arabinose), however, this characteristic occurred after only removing PPP1.

For utilization of both pentoses and hexoses, further investigation into reactions that participate in the 12 EMs has revealed that among the 12 EMs, 6 EMs utilize pyruvate dehydrogenase (GG13) catalyzed by the pyruvate dehydrogenase complex. This enzyme has been known to be inactive under anaerobic conditions. Therefore, deletion of the aforementioned reactions resulted in only 6 remaining EMs, two of which co-produced biomass and ethanol during the growth phase and the other four of which made only ethanol with or without maintenance energy.

The set of knockout genes corresponding to the set of deleted reactions included PPP1, OPM4r, ANA2, FEM3, TCA10, FEM2, and FEM7 are zwf, ndh, sfcA, maeB, ldhA, frdA, poxB, and pta (Table 4). An ethanologenic strain that contains the above set of knockout genes can efficiently convert individual pentoses and hexoses into ethanol according to the most efficient ethanol-producing pathways under anaerobic conditions.

TABLE 4

Targets of knockout genes of *E. coli*

| Deleted reactions | Corresponding deleted genes[a] | Corresponding encoded enzymes[a] |
|---|---|---|
| PPP1 | zwf | glucose 6-phosphate-1-dehydrogenase |
| OPM4r | ndh | NADH dehydrogenase II |
| ANA2 | sfcA/maeB | $NAD^+/NADP^+$-dependent malic enzyme |
| FEM3 | ldhA | D-lactate dehydrogenase |
| TCA10 | frdA | fumarate dehydrogenase |
| FEM2 | poxB | pyruvate oxidase |
| FEM7 | pta | phosphate acetyltransferase |

[a]Gene and enzyme annotations were taken from Ecocyc database that is available at ecocyc.org on the World Wide Web.

Example 9

Identification of Efficient Pathways for Co-Utilization of Pentoses and Hexoses As a test model, the co-utilization of xylose and glucose were investigated since the metabolism of both sugars exhibits opposite flux distribution. For growth on glucose, the carbon flux is directed from glycolysis to pentose phosphate pathway to synthesize precursors such as ribose-5-phosphate and erythro-4-phosphate. In contrast, for growth on xylose, the carbon flux is directed from pentose phosphate pathway to glycolysis to generate precursors such as glucose-6-phoshate and glyceraldehyde-3-phosphate.

For a model that considered the co-utilization of xylose and glucose, the elementary mode analysis identified 45,926 EMs, which were more than the combination of the total number of EMs that utilizes each sugar alone (Table 3). New EMs appeared due to the co-utilization of both glucose and xylose. Deletion of the same set of 7 reactions described above including PPP1, OPM4r, ANA2, FEM3, TCA10, FEM2, and FEM7 left only 36 EMs, 24 of which utilized either glucose or xylose individually as presented above. The other 12 co-utilized glucose and xylose. All of these remaining EMs were the efficient ethanol-producing pathways that achieved ethanol yield ranges of 0.36 to 0.51 g ethanol/g sugars.

Example 10

Design of an Efficient Pentose-Specific Ethanologenic E. coli Strain

Due to the effect of carbon catabolite repression when micro-organisms grow in mixtures of sugars that include glucose, the ethanol productivity is severely affected. In addition, different compositions of pentoses and hexoses from different sources of biomass also pose a challenge to control the efficient ethanol productivities. To address these problems, a system of microorganisms can be designed that ferment pentoses and hexoses from different compositions into ethanol simultaneously and efficiently. For example, one organism specializes in utilizing hexoses while the other specializes in utilizing pentoses. In this study, the efficient pentose-specific ethanologenic E. coli strain was used to consume pentoses because native E. coli can ferment a variety of pentoses. For hexoses, a variety of efficient ethanologenic strains were used such as the engineered E. coli strain proposed above that contains 8 chromosomal knockout genes, Z. mobilis, or S. cerevisiae. It is noted that both Z. mobilis and S. cerevisiae are native ethanologenic organisms that can only utilize hexoses.

An efficient pentose-specific ethanologenic E. coli strain was developed. The efficient ethanologenic strain previously designed with deleted genes zwf, ndh, sfcA, maeB, ldhA, frdA, poxB, and pta can be further engineered by removing key genes responsible for hexose transporters and degradation pathways. The hexoses targeted for disruption include glucose and mannose, which constitute the majority of biomass hydrolysates. Disruption of glucose transporters and degradation pathways involves deleting both a part of glucose phosphotransferase system (ptsG) and glucose kinase (glk). Furthermore, partial deletion of mannose phosphotransferase system (manX) diminishes the degradation of mannose. Since the mannose phosphotransferase system is not specific and able to metabolize not only mannose but also glucose, disruption of manX eliminates potential degradation of glucose as well. Thus, deleting the above-indicated set of chromosomal genes as well as ptsG, glk, and manX disrupted the majority of hexose degradation pathways of E. coli. Thus, an efficient ethanologenic E. coli strains that can favorably ferment pentoses has the following set of knockout genes zwf, ndh, sfcA, maeB, ldhA, frdA, poxB, pta, ptsG, glk, and manX.

Example 11

Strain Construction

TCS083 is derived from TCS062, which has six knockout genes including zwf, ndh, sfcA, maeB, ldhA, and frdA (Trinh et al., 2006, supra). TCS083 contains two additional deleted genes involved in the acetate-producing pathway including poxB and pta. From the model prediction, TCS083/pLOI297, which contains 8 chromosomal knockout genes as well as two cloned genes from Zymomonas mobilis (pdc$_{ZM}$ and adhE$_{ZM}$) can convert individual pentoses and hexoses into ethanol at high yields. CT1101 is a derivative of TCS083 that possesses three additional deleted genes including ptsG and glk, involved in the glucose degradation pathway, and manX, involved in the mannose degradation pathway. CT1101 is designed as a pentose-specific ethanologenic E. coli strain. PCR amplification of the deleted genes in TCS083 and CT1101 was performed using the primers shown in Table 2. If a particular gene was deleted, the band size of the mutant was smaller than that of the wild type. Results of the PCR confirmed that both TCS083 and CT1101 had all the appropriate genes knocked-out and completely removed from their chromosomes. All bands appeared at the expected sizes.

Example 12

Strain Characterization for Ethanol Production on Individual Pentoses and Hexoses To verify the strain performance, TCS083/pLOI297 was characterized and compared with MG1655/pLOI297 as a control on xylose and glucose, individually, in controlled batch bioreactors. The tested strain, TCS083/pLOI297, contains 8 knockout genes including zwf, frdA, ldhA, sfcA, maeB, ndh, poxB and pta and two cloned genes pdc$_{ZM}$ and adhE$_{ZM}$ from Zymomonas mobilis introduced via the pLOI297 plasmid.

Figure 4:
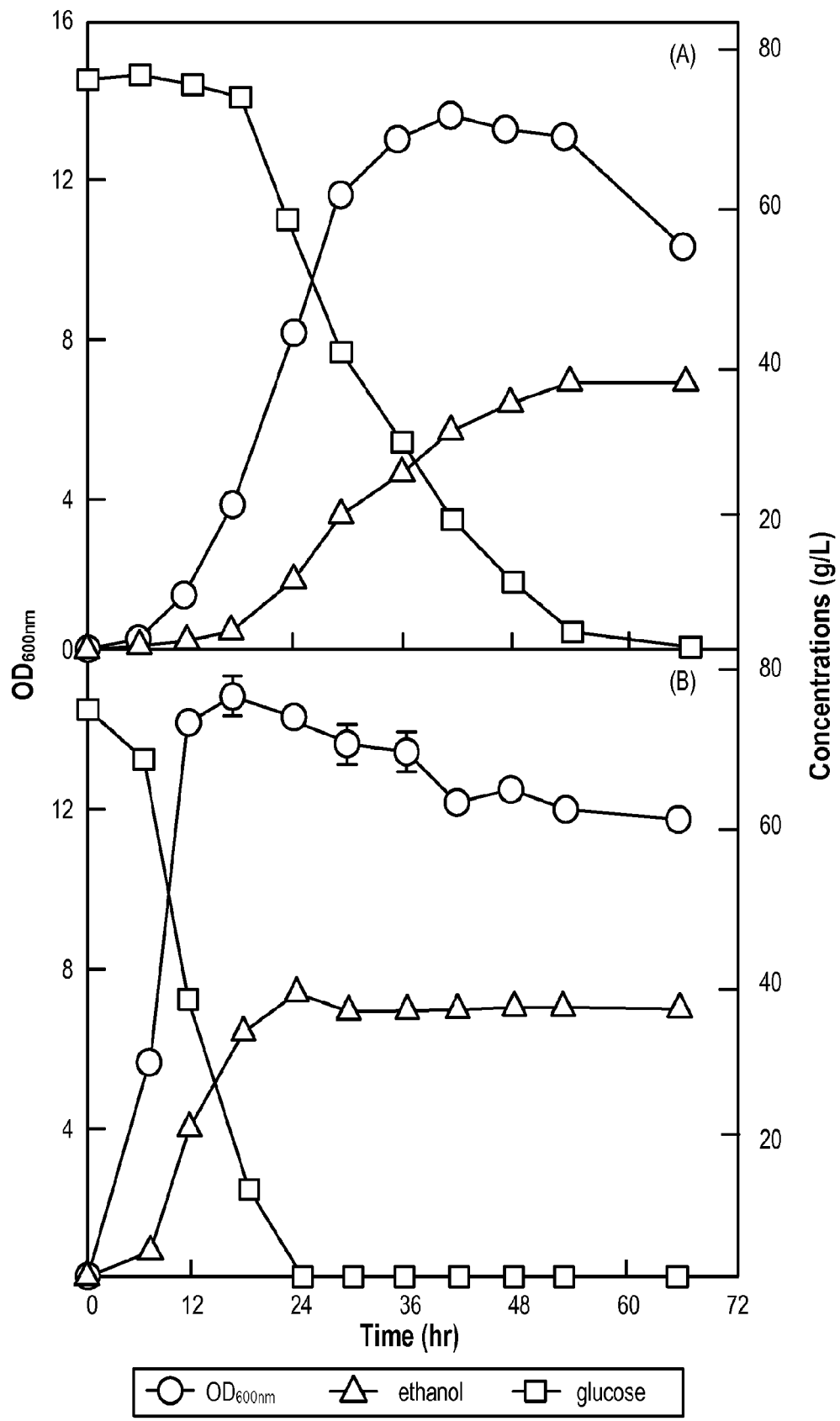
FIG. 4 shows graphs that demonstrate the performances of (A) TCS083/pLOI297 and (B) MG1655/pLOI297 in terms of growth, ethanol production, and glucose consumption conducted in controlled batch bioreactors using 80 g/L glucose.

FIG. 4 demonstrates growth performances of TCS083/pLOI287 and the wild type MG1655/pLOI297 on 80 g/L glucose. MG1655/pLOI297 achieved an ethanol yield of 0.49±0.01 (g ETOH/g glucose) and an ethanol titer of 37.61±0.31 g/L. Under identical growth conditions, TCS083/pLOI297 achieved a 6.1% performance improvement with an ethanol yield of 0.52±0.01 (g ETOH/g glucose) and an ethanol titer of 39.92±0.61 (g/L). MG1655/pLOI297 consumed glucose at a faster rate than TCS083/pLOI297. It took 54 hours for TCS083/pLOI297 to consume glucose completely, but only 24 hours for MG1655/pLOI297. The lower ethanol yield of MG1655/pLOI297 is attributable to the production of by-products such as succinic acid (3.6 g/L), lactic acid (2.53 g/L) and acetic acid (0.75 g/L). TCS083/pLOI297 had a minimal amount of secreted fermentative acids because most of the fermentative acid pathways were deleted or disabled.

Figure 5:
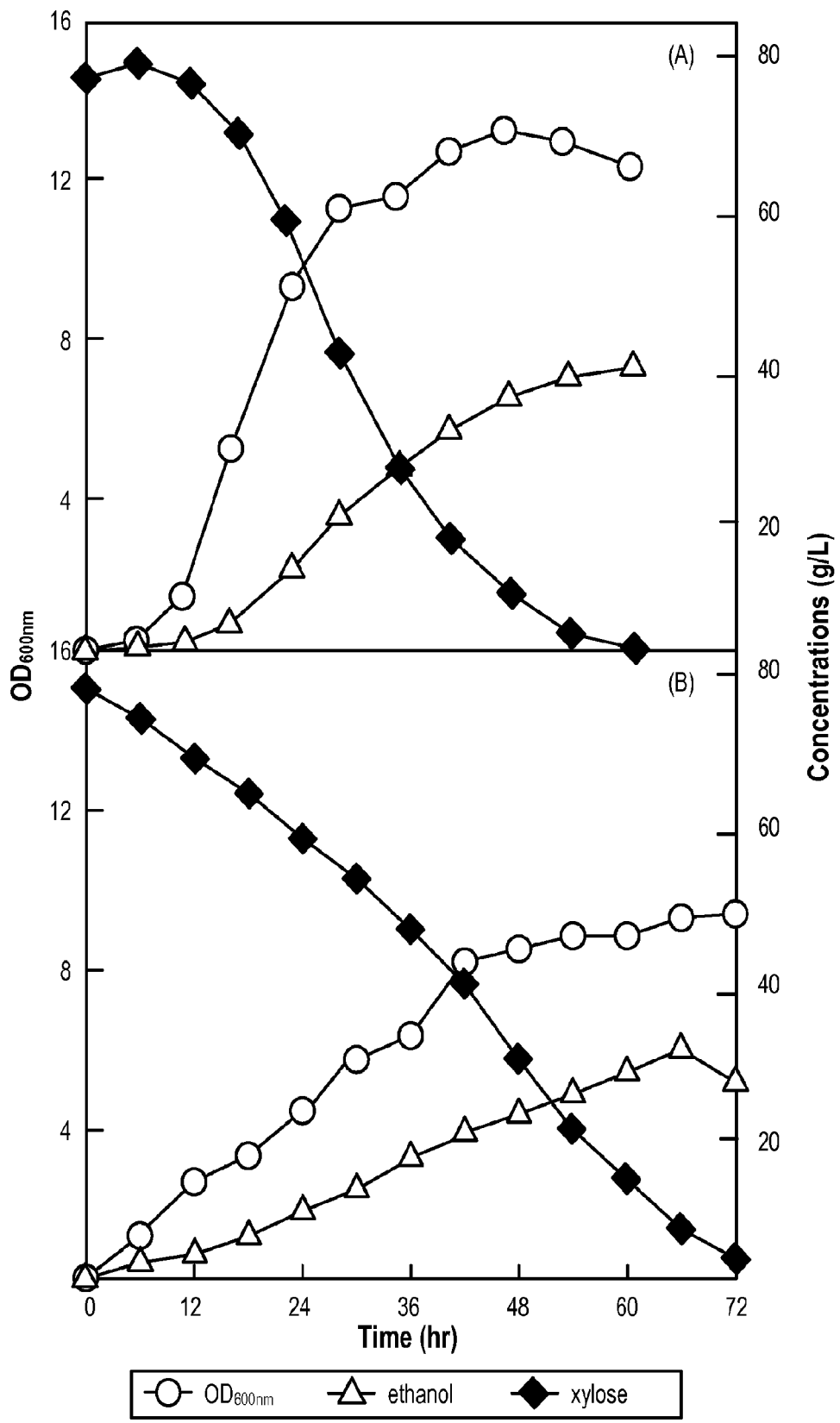
FIG. 5 shows graphs that demonstrate the performances of (A) TCS083/pLOI297 and (B) MG1655/pLOI297 in terms of growth, ethanol production, and xylose consumption conducted in controlled batch bioreactors using 80 g/L xylose.
Figure 6:
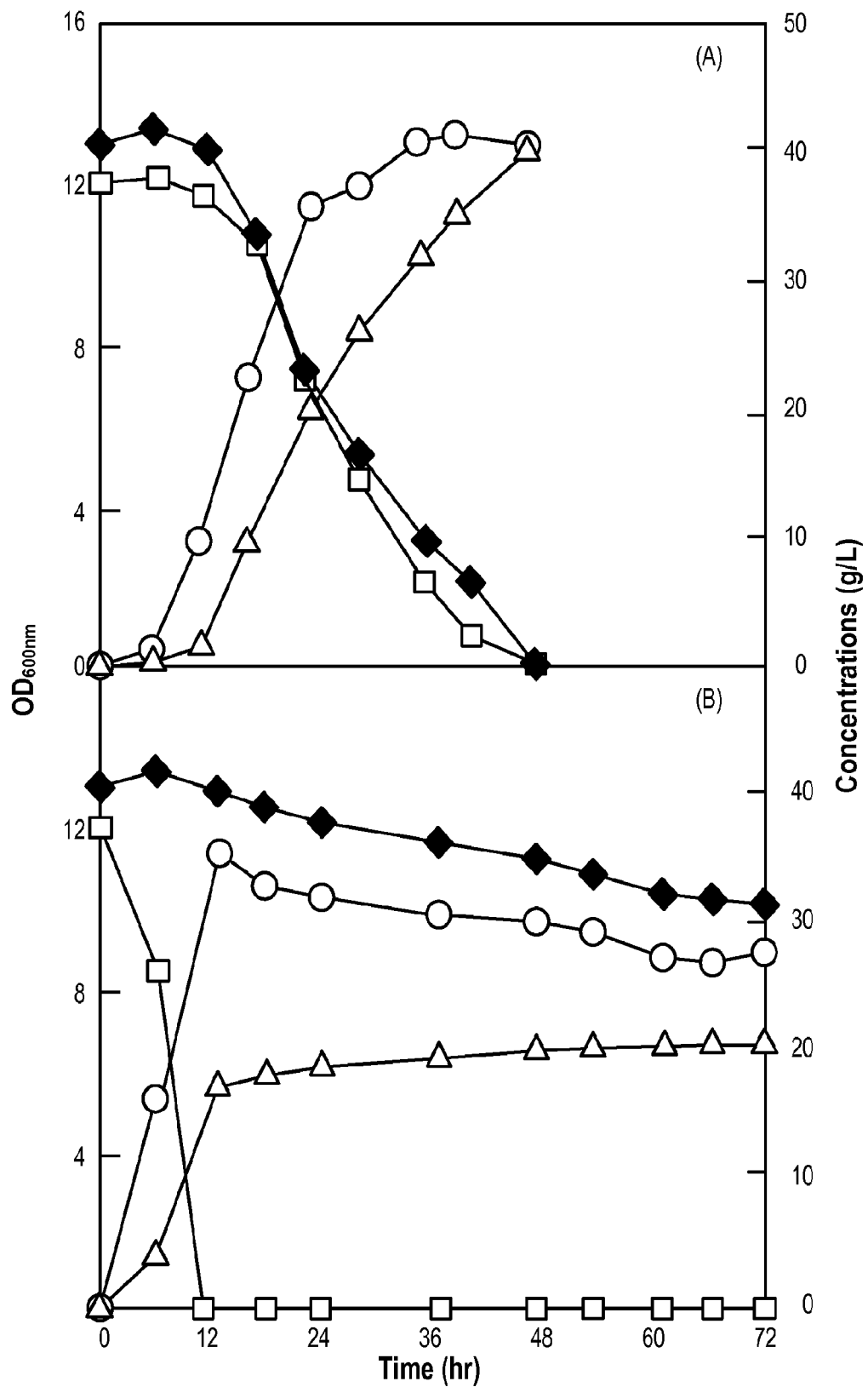
FIG. 6 shows graphs that demonstrate the performances of (A) TCS083/pLOI297 and (B) MG1655/pLOI297 in terms of growth, ethanol production, and consumption of xylose and glucose conducted in controlled batch bioreactors using mixtures of 40 g/L xylose and 40 g/L glucose.

MG1655/pLOI297 exhibited a completely different phenotype when grown on 80 g/L xylose. The xylose consumption rate was slower than the glucose consumption rate. As shown in FIG. 5, after 72 hours, MG1655/pLOI297 had not completely consumed all xylose, with 4% remaining MG1655/pLOI297 achieved an ethanol yield of 0.46±0.01 (g ethanol/g xylose) and an ethanol titer of 34.17±2.35 (g/L). Different from MG1655/pLOI297, TCS083/pLOI297 had similar phenotypes for growth on either 80 g/L glucose or 80 g/L xylose. TCS083/pLOI297 consumed all the xylose after 54 hours. TCS083/pLOI297 achieved a higher ethanol yield of 0.50±0.01 (g ethanol/g xylose) and a higher ethanol titer of 40.56±0.36 (g/L). Similar to growth on glucose, MG1655/pLOI297 reached a lower ethanol yield and titer than did TCS083/pLOI297, likely due to the production of by-products such as succinic acid (3.71 g/L), lactic acid (2.3 g/L), and acetic acid (1.57 g/L). The secretion of a high concentration of acetic acid also inhibited the cell growth of MG1655/pLOI297 and, hence, contributed to the slow xylose consumption rate.

Example 13

Figure 8:
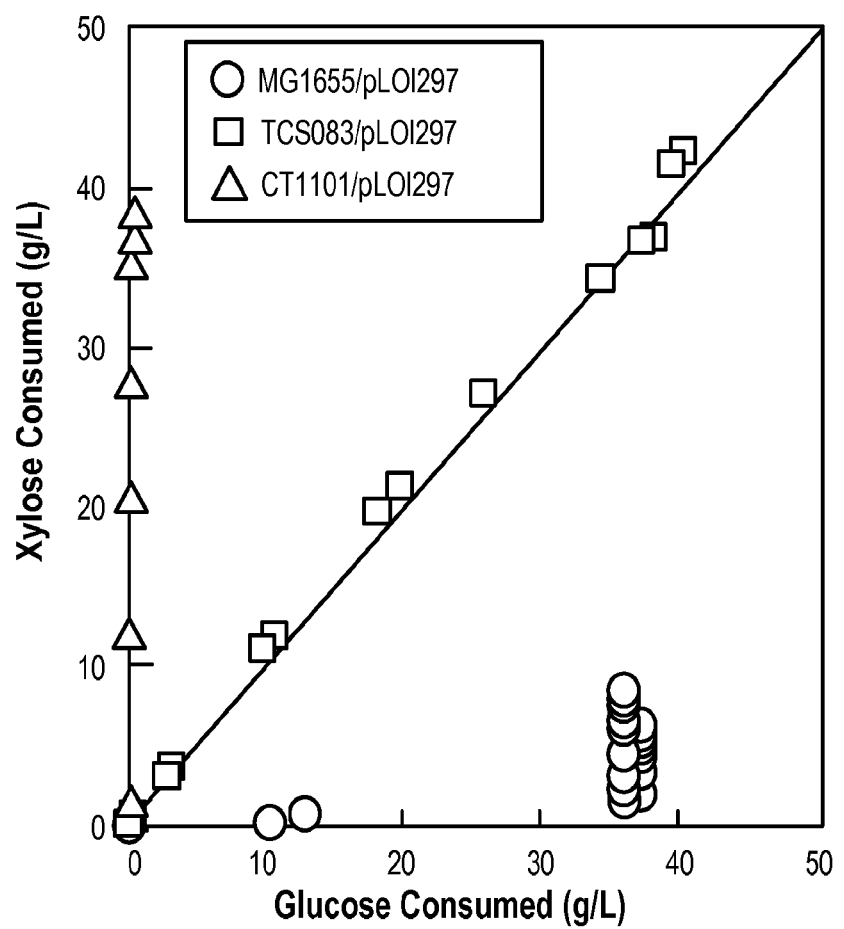
FIG. 8 shows a graph that demonstrates the parametric profile of consumption of glucose and xylose of MG655/pLOI297, TCS083/pLOI297, and CT1101 conducted in controlled batch bioreactors using mixtures of 40 g/L xylose and 40 g/L glucose.

Strain Characterization for Ethanol Production on Mixtures of Pentoses and Hexoses The strains performance for ethanol production also was investigated on a mixture of 40 g/L glucose and 40 g/L xylose in controlled batch bioreactors. MG1655/pLOI297 consumed first glucose and then xylose in a sequential manner. As shown in FIG. 8, it only took MG1655/pLOI297 about 12 hours to completely consume glucose but 72 hours to consume 20% of 40 g/L xylose. MG1655/pLOI297 achieved an ethanol yield of 0.44±0.02 (g ethanol/g sugar) and an ethanol titer of 19.27±0.82 (g/L). TCS083/pLOI297 outperformed MG1655/pLOI297 because it could simultaneously consume both glucose and xylose and completely utilize all sugars after 48 hours. TCS083/pLOI297 achieved a higher ethanol yield of 0.50±0.01 (g ethanol/g sugars) and a higher ethanol titer of 39.50±0.21 (g/L).

Example 14

Figure 7:
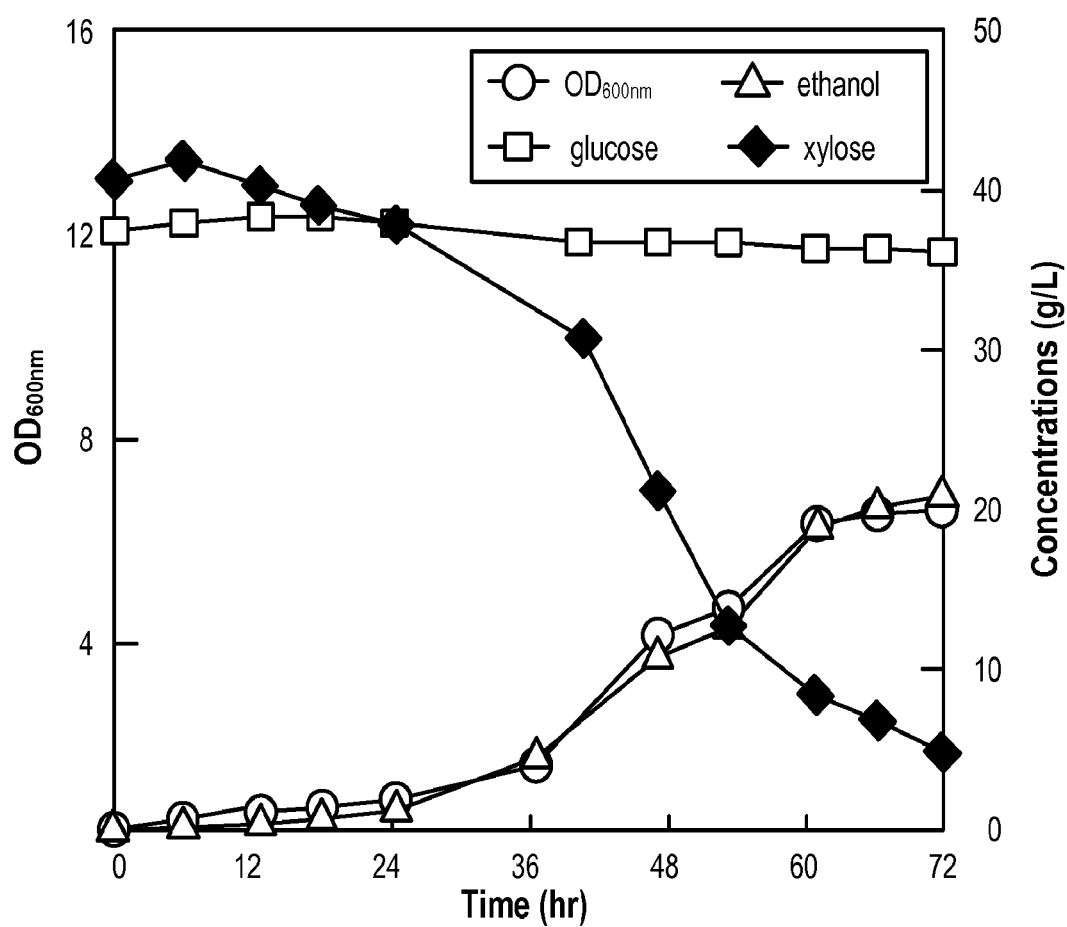
FIG. 7 shows a graph that demonstrates the performance of CT1101/pLOI297 in terms of growth, ethanol production, and consumption of xylose and glucose conducted in controlled batch bioreactors using mixtures of 40 g/L xylose and 40 g/L glucose.

Characterization of the Efficient Pentose-Specific Ethanologenic E. coli Strain for Ethanol Production on Mixtures of Pentoses and Hexoses CT1101/pLOI297 was designed as an efficient pentose-specific ethanologenic E. coli strain. It contains 11 chromosomal gene knockouts that allow it to favorably utilize pentoses and that operate according to the most efficient ethanol-producing pathways. The performance of CT1101/pLOI297 for ethanol production was examined on mixtures of xylose and glucose. As shown in FIG. 7, CT1101/pLOI297 exhibited the expected growth phenotypes. The strain could only consume xylose but not glucose. CT1101/pLOI297 achieved an ethanol yield of 0.51±0.00 (g ethanol/g sugars) and an ethanol titer of 19.97±0.12 (g/L). The xylose consumption rate of CT1101/LOI297 was slightly slow because the strain exhibited a lag growth during the first 24 hours, which, therefore, resulted in a lower biomass than TCS087/pLOI297 and MG1655/pLOI297.

Example 15

Investigation of Utilization Mode of Xylose and Glucose

To better examine the mode of utilizing a mixture of glucose and xylose, a parametric plot was constructed that shows the consumption of glucose and xylose. FIG. 8. Data points located on the x-coordinate assume that only glucose is utilized, while data points located on the y-coordinate assume that only xylose is consumed. Sugar consumption profiles of MG1655/pLOI297 contain data points that first appeared on the x-coordinate then on a vertical line parallel to the y-coordinate. This profile suggests that glucose is first consumed followed by xylose in a sequential manner. Different from MG1655/pLOI297, CT1101/pLOI297 contains data points only along the y-coordinate. This profile suggests that CT1101/pLOI297 only utilizes xylose. TCS083/pLOI297 exhibited a very interesting profile with all data points located on the diagonal line, indicating that both xylose and glucose are utilized simultaneously.

Example 16

Production of TSC099

Strain Construction.

Based on the model prediction, we have constructed the strain TCS099 that contains 9 gene knockouts at zwf, ndh, mdh, sfcA, maeB, frdA, pta, poxB, ldhA. TCS099 was derived from the efficient ethanologenic strain, TCS083, described above. TCS099 differs from TCS083 in that TCS099 contains an additional knockout gene, mdh, encoding a malate dehydrogenase polypeptide. All chromosomal knockout genes in TCS099 were verified by PCR amplification.

The mdh gene knockout was carried out by P1 generalized transduction as described herein. TCS083 was infected with P1 lysate prepared from the donor strain, BW25113 mdh::kan+. After the transductant was isolated with the kanamycin selection marker, its kanamycin gene was removed by using the temperature sensitive helper plasmid, pFT-A. The knockout of the mdh gene was verified by using PCR with primers located outside of the undeleted portion of the structural gene. The sequences of the primers were 5'-CTG GAG ACG ATG GAT CAG GT-3' (forward; SEQ ID NO:23) and 5'-CAC CAC CTG TTG GAA TGT TG-3' (reverse; SEQ ID NO:24). Plasmid pLOI297 (ATCC68239), which contains the pyruvate decarboxylase and alcohol dehydrogenase genes from Zymomonas mobilis, was obtained from the American Type Culture Collection (ATTC).

Metabolic Evolution.

The experiments were conducted aerobically in 250 mL shake flasks with a working volume of 100 mL of minimal medium containing 20 g/L of glycerol. The metabolic evolution was done by serial dilution. Metabolic evolution started with a single colony picked from a petri dish freshly spread from a culture stock. The growth conditions were set at 225 rpm and 37° C. At each serial dilution step, cell cultures with concentrations of $10^8$-$10^9$ cells/ml in the exponential growth phases were transferred to fresh medium. The initial cell cultures started with cell number concentrations of $10^5$-$10^6$ cells/mL. To achieve the exact growth conditions for each transfer, fresh medium was placed in the same environment of the cell cultures at least two hours before inoculation. Two serial dilutions were performed every day. Serial dilution was stopped when specific growth rates reached stable values after 50 culture transfers.

Three independent replicates were performed for metabolic evolution of each strain. At least four data points were collected to measure the specific growth rates. In all cases, linear regression coefficients resulting from calculating slopes of $\ln(OD_{600nm})$ against time (hr) were greater than 0.99. For every five transfers, samples of cell cultures were stored at −80° C.

Results.

Figure 12:
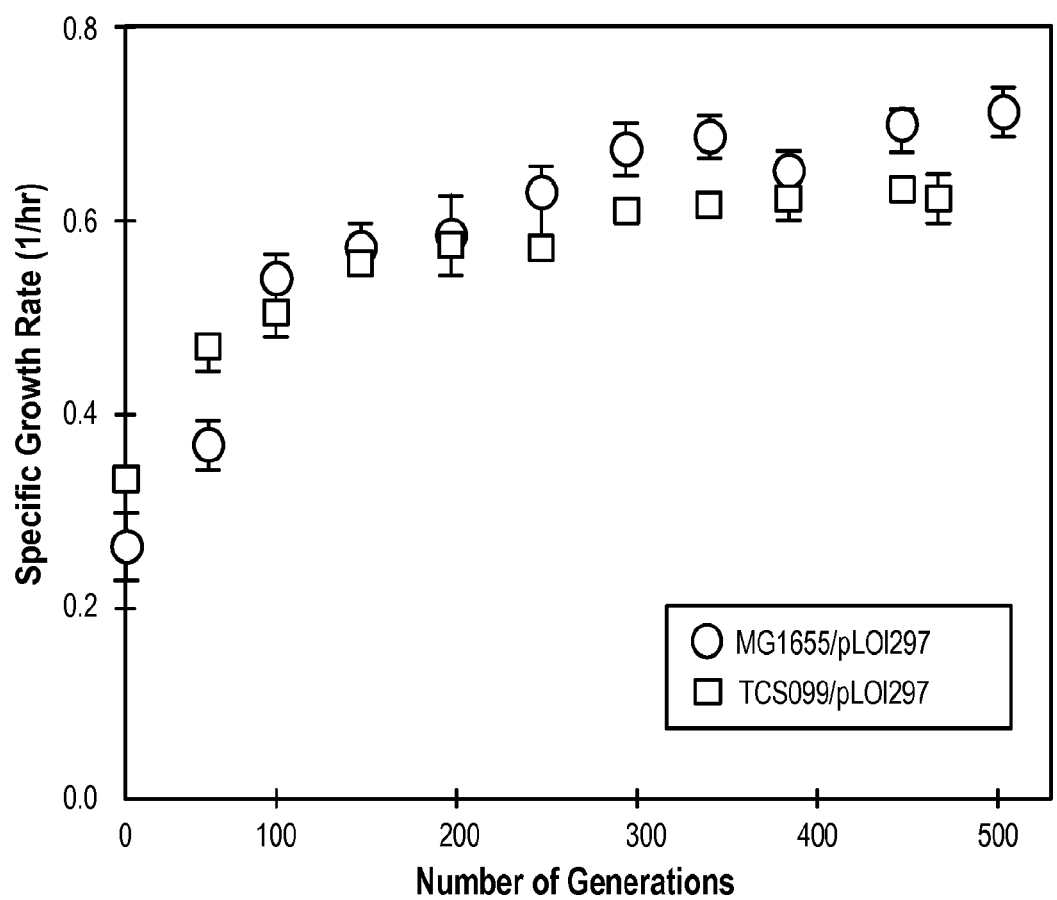
FIG. 12 is a graph showing the dynamic changes in specific growth rates of the wild type MG1655/pLOI297 and TCS099/pLOI297 through metabolic evolution.

Metabolic evolution was performed for both the wild type MG1655/pLOI297 and the mutant TCS099/pLOI297 under identical growth conditions. At the beginning of metabolic evolution, the wild type starts with a specific growth rate of 0.27±0.06 (1/hr) while the mutant begins with 0.33±0.02 (1/hr). For both the wild type and the mutant, improvements in specific growth rates took place at a fast rate during the first 150 generations of metabolic evolution (FIG. 12). The improvement rates slowed down between 150 and 350 generations. The specific growth rates became stabilized between 350 and 500 generations. At the end of metabolic evolution experiments, the specific growth rate of the wild type reached 0.65±0.02 (1/hr) and showed a 2.40 fold increase. Exhibiting a similar trend, the specific growth rate of the mutant achieved 0.65±0.00 (1/hr) and exhibited a 1.74 fold increase.

Each data point in FIG. 12 represents a mean plus 1 standard deviation of three replicate independent experiments conducted under identical growth conditions. It is interesting to observe that the error bars become smaller toward the end of metabolic evolution for both strains. This result indicates that the variants of each evolved strain appear to converge to the same specific growth rate at the end of metabolic evolution. In order to differentiate the evolved strain from its parent and distinguish variants among different replicate experiments, the following designations were used for the strain name: "e#rep$", where "#" refers to the culture transfer number and "$" designates the replicate number. For instance, TCS099/pLOI297 is the parent strain harboring the plasmid pLOI297, while TCS099 e50rep1/pLOI297 is the evolved strain derived from TCS099/pLOI297. The evolved strain in this example was isolated after 50 rounds of transfer (e50) from the first replicate (rep1).

Strain Performance.

Under identical growth conditions, the performance of several different strains including the wild type MG1655/pLOI297, the mutant TCS099/pLOI297, and their evolved derivatives isolated at the end of metabolic evolution was characterized. The basis for the growth condition was set at kLa=0.3 (1/min).

Figure 13:
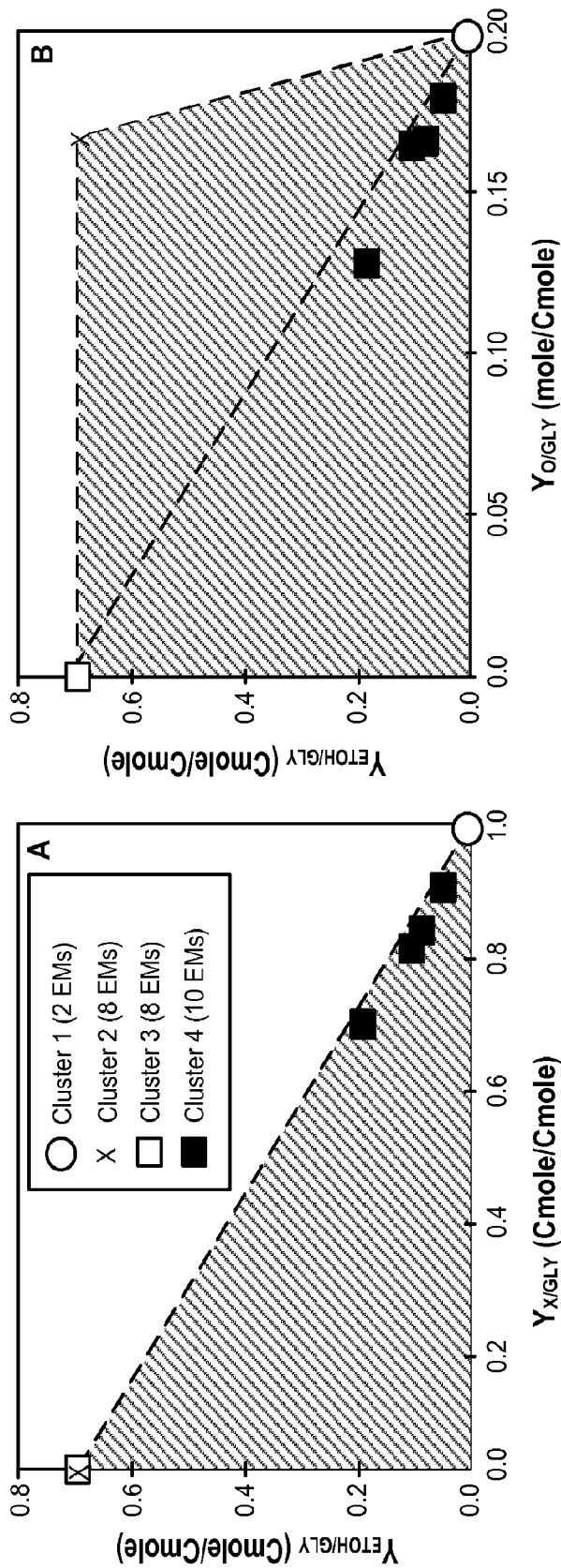
FIG. 13 is a graph showing the inverse relationship of ethanol yields and biomass yields (A) and of ethanol yields and oxygen yields (B).

During the growth associated phase, pathways that make biomass and ethanol are processes that compete for the same carbon source derived from glycerol. As shown in FIG. 13A, ethanol yields are inversely proportional to biomass yields. This inverse relationship also applies to oxygen and ethanol yields (FIG. 13B).

Under completely aerobic growth conditions, the mutant, TCS099/pLOI297, can produce biomass yield as high as 0.77 g biomass/g glycerol and ethanol yield as low as 5.10 mg ethanol/g glycerol. However, the TCS099/pLOI297 mutant potentially can produce a yield of ethanol that approaches the theoretical yield of ethanol (0.50 g ethanol/g glycerol) under microaerobic conditions.

Example 17

Production of AFF01

To select for a robust mutant E. coli strain, an overnight culture of E. coli TCS083 was treated with 100 mg/ml of a mutagen, nitrosoguanidine (NTG), and inoculated into a chemostat. The chemostat culture was carried out in a 125 ml aerobic shake flask with a working volume of 100 ml and operated at a dilution rate of 0.1 $hr^{-1}$. Temperature was controlled at 37° C., and the stirring rate was set at 100 rpm. pH in the culture was not controlled. The feed medium was LB supplemented with 2% glucose, 2% xylose and various concentrations of acetic acid and furfural. The concentration of acetic acid was at 5 g/L initially and was shifted to 10 g/L after 8 days and to 15 g/L after 13 day. After 15 days, 1 g/L of furfural was added to the feed medium. The concentration of acetic acid (15 g/L) and furfural (1 g/L) was maintained for approximately 30 days. At the end, a single clone was isolated and designated AFF01. AFF01 and its parent, TCS083, were then compared for their resistance capacity against acetic acid, furfural and other inhibitors present in hydrolysates. The fermentation performance of both strains was also tested under acetic acid challenge and furfural challenge.

Figure 14:
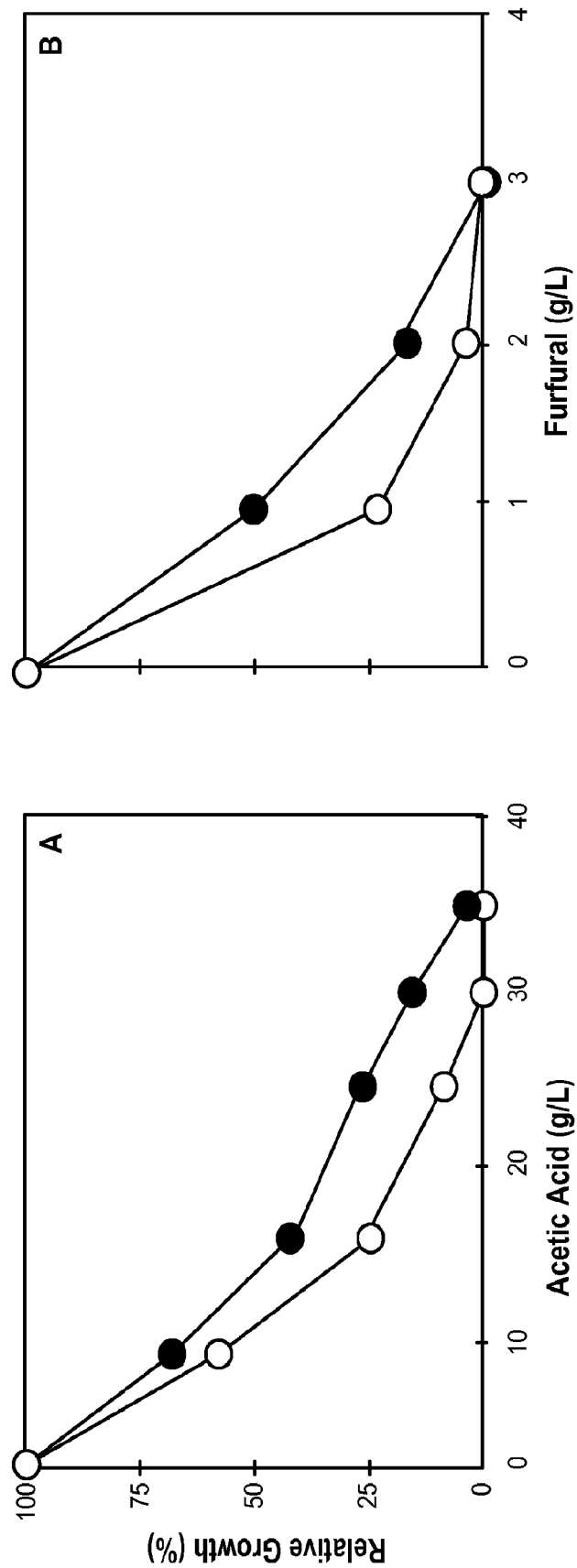
FIG. 14 are graphs showing the inhibition of *E. coli* TCS083 (open) and AFF01 (shaded) in the presence of acetic acid (Panel a) or furfural (Panel b).
Figure 15:
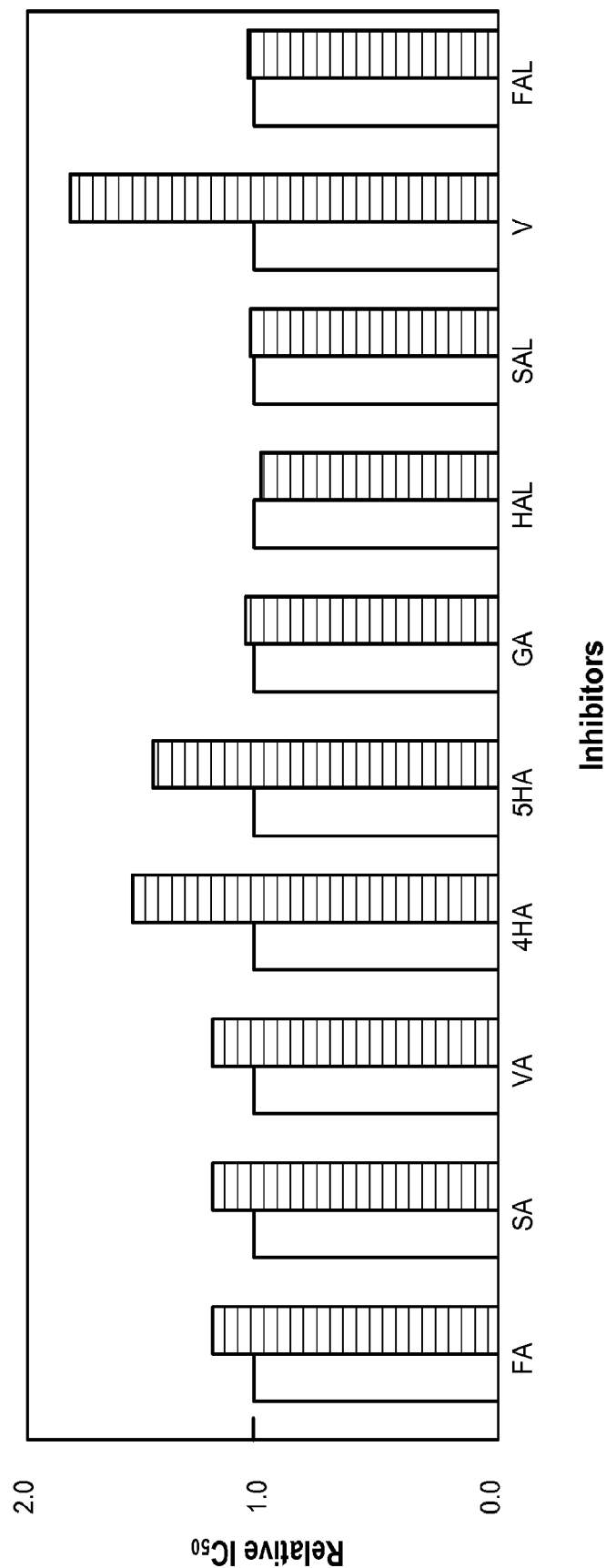
FIG. 15 is a graph showing the relative inhibitory concentration at 50% reduced growth rate (IC50) of inhibitors present in hydrolysates for *E. coli* TCS083 (open) and AFF01 (shaded). FA: Formic acid; SA: Syringic acid; VA: Vanillic acid; 4HA: 3,4-Hydroxybenzoic acid; 5HA: 3,5-Hydroxybenzoic acid; GA: Gallic acid; HAL: Hydroxybenzaldehyde; SAL: Syringaldehyde; V: Vanillin; FAL: Furfuryl alcohol.
Figure 16:
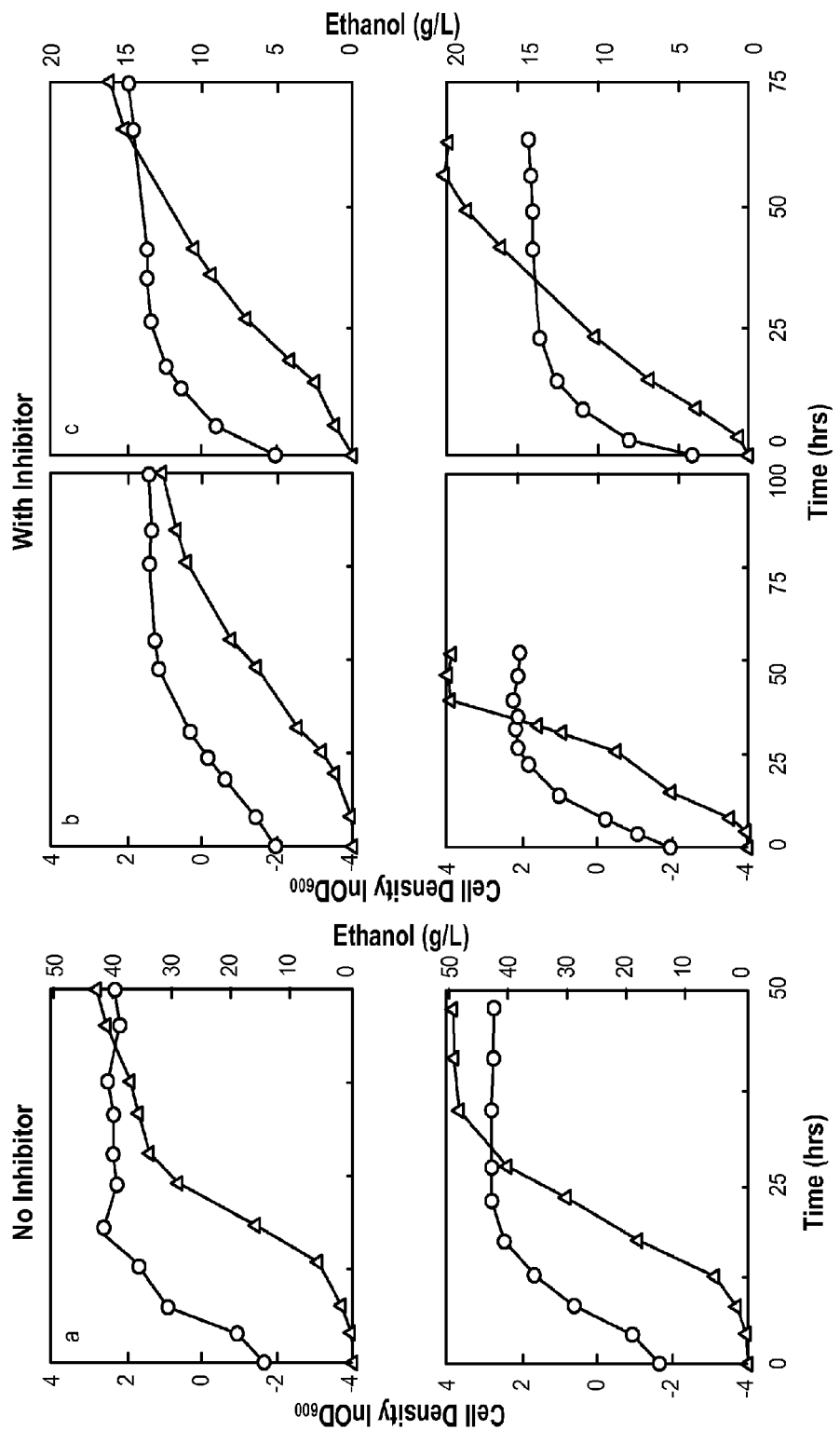
FIG. 16 are graphs showing the time profiles for cell density (circle) and ethanol (triangles) for TCS083/pLOI297 (top) and for AFF01/pLOI297 (bottom) in anaerobic batch bioreactor containing LB complex medium with 50 g/l (each) mixed glucose and xylose and no inhibitor (a) with 40 g/L mixed glucose and xylose and 15 g/L acetic acid (b), with 40 g/L mixed glucose and xylose and 1 g/L furfural (c).

The AFF01 mutant exhibited more tolerance against acetic acid and furfural than its parent TCS083 (see FIG. 14). AFF01 also showed an increase in resistance against other acidic-type inhibitors (FIG. 15). Moreover, fermentation in the presence of acetic acid or furfural demonstrated that the mutant outperformed its parent in ethanol titer, productivity and yield. The results are shown in FIG. 16.

Section B. Yeast Production

Example 1

Increasing Resistance to Inhibitors

Inhibitors are present in corn stover hydrolysate and, thus, an ethanologenic organism adapted to these inhibitors is required. While an adaptation process frequently involves serial dilution of growing cultures, this is a very inefficient process as the culture spends much of the time at suboptimal growth rates. A continuous culture is far more efficient since the culture is maintained at a constant specific growth rate. The recently developed cytostat process (Kacmar et al., 2006, J. Biotechnol., 126(2):163-72) maintains a culture growing at the maximum growth rate supported by the feed medium. This is accomplished by maintaining the cell number concentration at a sufficiently low level such that the cells consume negligible nutrients from the feed medium. When an inhibitor is added to the feed medium at a desired concentration, the culture is grown continuously at the culture's maximum rate in the presence of this inhibitor. Once a mutant capable of growing more quickly in the presence of the inhibitor is generated within the population, the mutant will rapidly overtake the culture as the dilution rate of the culture automatically increases to compensate.

Cytostat experiments were used to produce the mutant S. cerevisiae strain, AG3, disclosed herein. After 84 h of culturing in a medium containing 10 g/L of total acetate, the feed medium was changed to 20 g/L. As the acetate concentration increased, the dilution rate slowly decreased as the cell number concentration was maintained at 100,000 cells/ml. At approximately 145 h, there was an increase in the cell number concentration, automatically coupled with an increasing dilution rate. At 155 h, AG3 was isolated from the bioreactor effluent stream. Through comparative genome hybridization using cDNA microarrays, it was determined that mutant strain AG3 had an amplified lpp1 gene as compared to the wild type s288c strain.

Example 2

Characteristics of AG3

Figure 9:
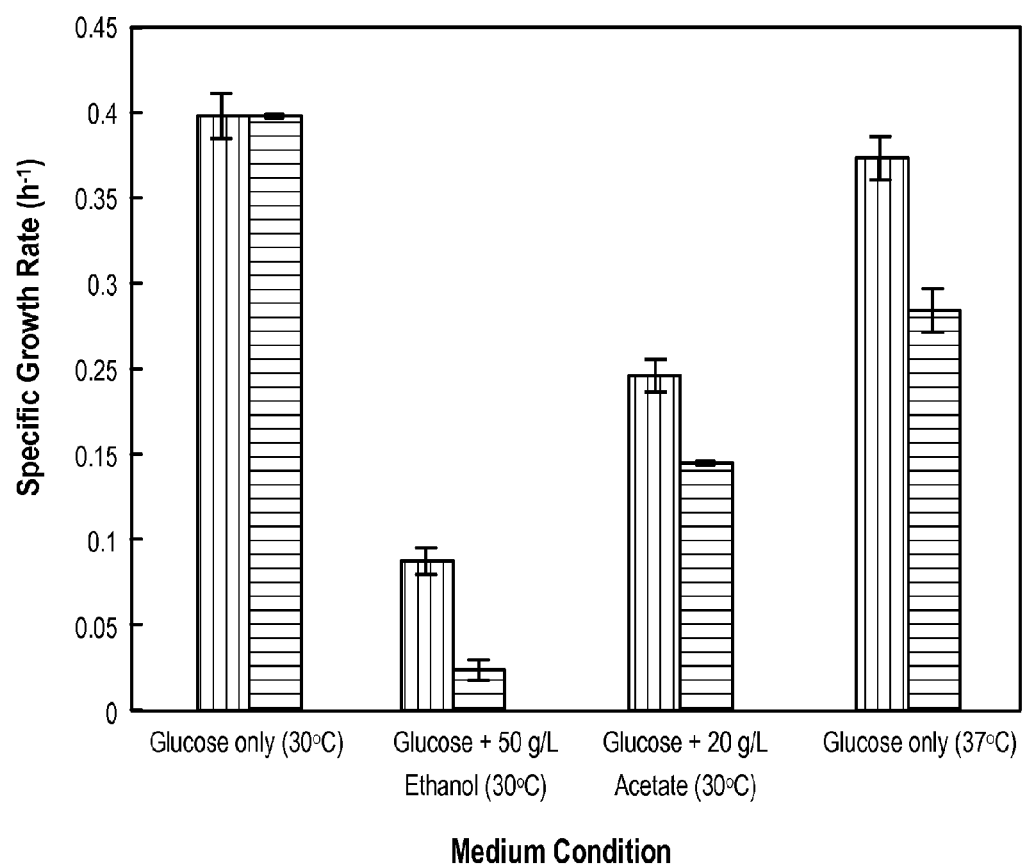
FIG. 9 shows a graph that demonstrates the growth rate dependence of *S. cerevisiae* on growth medium. Mutant strain AG3 (light bars) shows increased growth rates in the presence of both ethanol and acetate as well as at elevated temperatures as compared with the wild type s288c (dark bars).

As shown in FIG. 9, the AG3 strain retained 19.9% of its specific growth rate when grown purely on glucose in the presence of 50 g/L ethanol, 65% in the presence of 20 g/L acetate, and 92.5% at the elevated temperature of 37° C.

Figure 10:
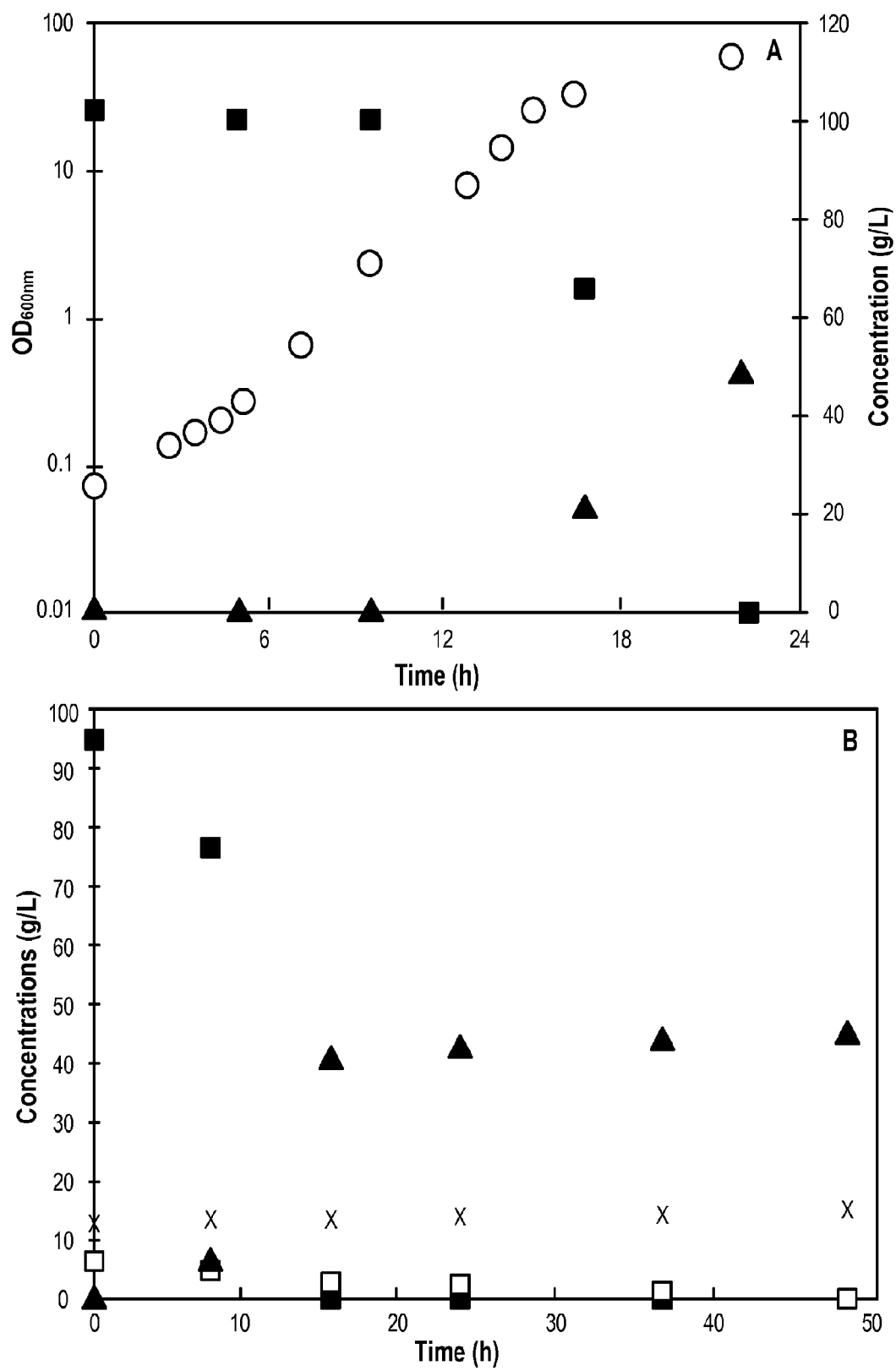
FIG. 10 shows a graph that demonstrates ethanol production by *S. cerevisiae* AG3 using YPD medium (100 g/L glucose, 20 g/L peptone, 10 g/L yeast extract) (Panel A) or using medium containing 95 g/L glucose (■), 5 g/L galactose (□), and 10 g/L acetate (×) (Panel B). In both experiments, the optical density (◇) increased rapidly as all of the sugar was consumed and 45 and 47 g/L of ethanol (▲) was produced in the two experiments respectively. The presence of the 10 g/L acetate in Panel B did not prevent the high ethanol titer from being achieved quickly.

These retentions of growth rate were much higher than the 7.3%, 37.5%, and 72.5% observed in wild type S. cerevisiae for the same respective medium conditions. The improved growth characteristics, therefore, included increased resistance to the deleterious effects of high acetate concentrations, high ethanol concentrations and heat. Since ethanol production is tied to growth in S. cerevisiae, improved growth leads to a faster process without losing yield. As seen in FIG. 10, AG3 was capable of producing high concentrations of ethanol in relatively short periods of time. 45 g/L of ethanol was produced in 22 hours, even when using an inoculum of less than 0.05 g cell dry weight/L (FIG. 10A). FIG. 10B demonstrates that the same ethanol titer was achieved even in the presence of 10 g/L acetate as an inhibitor and even when the hexose composition was modified with a small portion of galactose.

Figure 11:
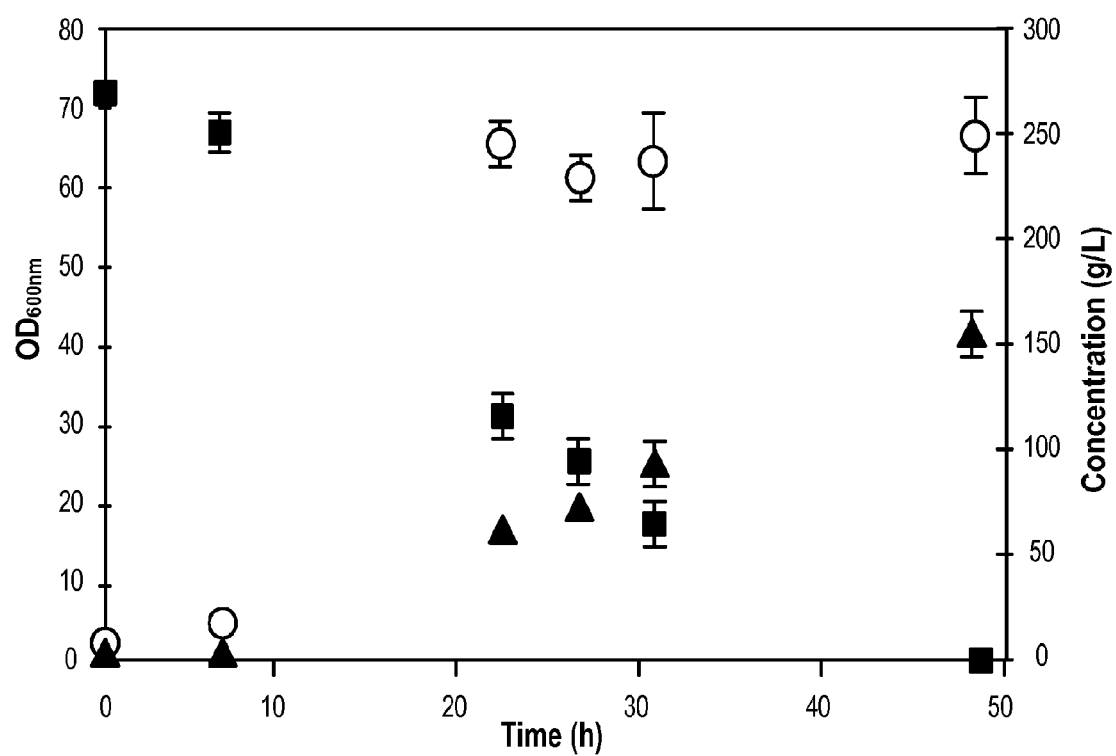
FIG. 11 shows a graph that demonstrates ethanol production by *S. cerevisiae*. AG3 is shown using enriched YPD medium (266 g/L glucose, 20 g/L peptone, 10 g/L yeast extract). All of the glucose (■) is consumed in less than 50 hours producing an ethanol (▲) titer over 100 g/L. The optical density (◇) remains unchanged on the second day of the experiment demonstrating that biomass production can be decoupled from ethanol production.

Experiments in minimal medium suggest that strain AG3 produces ethanol at the theoretical yield when the sugar converted to biomass is accounted for through the method of Alper et al. (2006, Science, 314:1565). As seen in FIG. 11, strain AG3 has been shown to produce ethanol in a non-growth associated manner. Experiments also demonstrated the high ethanol tolerance of strain AG3 as, in addition to the resistance to acetate, the yeast produced ethanol concentrations higher than 100 g/L in the absence of an observable reduction in growth.

Example 3

Conversion of Mixed Sugars

Fermentation of S. cerevisiae strain AG3 was capable of rapidly utilizing all available 6-carbon sugars at 91% of theoretical yield. In these experiments, a high ethanol titer was achieved from mixed 6-carbon sugars using S. cerevisiae AG3. The fermentation performance of the S. cerevisiae strain is summarized in Table 5.

Example 4

Mixed Sugar Fermentation in the Presence of Acetate Inhibition

S. cerevisiae strain AG3 showed impressive resistance to inhibitors such as acetic acid. Consequently, the strain rapidly and efficiently consumed all 6-carbon sugars provided within a short period of time. The same increase in ethanol yield and productivity was observed as that in Example 17. Not only was the AG3 strain resistant to acetic acid, but it also tolerated a higher level of ethanol than did the parental wild type strain.

Example 5

Diploidization of AG3

Diploidization of a haploid yeast strain is achieved by crossing the AG3 haploid strain with a haploid strain of the opposite mating type. Using subsequent sporulation and tetrad analysis, two homozygous haploid strains of opposite mating types can be isolated, which, upon crossing, results in a homozygous diploid version of AG3.

Alternately, a ura mutant and a petit mutant from AG3 are obtained. The ura mutant can grow only when uracil is added to the growth medium, while the petit mutant has a defect in the mitochondria and cannot grow on substrates requiring respiration such as glycerol or acetate. When a mixture of the two mutants is grown on acetate plates without uracil supplementation, diploids are selected directly. The frequency of such diploidization events is increased when the two mutants are converted into protoplasts and brought into close contact before plating on selective plates. The ura mutation are then

TABLE 5

Fermentation performance of S. cerevisiae strain AG3

| S. cerevisiae Fermentation Performance Results | Results reported as | Test 1 (Mixed Sugars) | Test 1 + Standard Deviation | Test 2 (Inhibitors) | Test 2 + Standard Deviation | Test 3 (Elevated levels) |
|---|---|---|---|---|---|---|
| Starting cell concentration | g Dry cell mass/liter | 0.186 | 0 | 0.196 | 0 | 0.202 |
| Fermentation vessel | Flask, fermentor | Flask | — | Flask | — | Flask |
| Fermentation process | Batch, fed-batch, continuous | Batch | — | Batch | — | Batch |
| Start volume | ml | 100 | — | 100 | — | 100 |
| Media type | | Complex | — | Complex | — | Complex |
| Fermentation Temperature | ° C. | 30 | — | 30 | — | 30 |
| Fermentation pH$_{initial}$ | pH | 6.62 | 0 | 6.67 | 0 | 6.66 |
| Fermentation pH$_{final}$ | pH | 4.81 | 0.03 | 5.48 | 0.06 | 5.59 |
| pH control | Yes/No | No | — | No | — | No |
| Fermentation time | Hours | 32 | — | 40 | — | 50 |
| Ethanol concentration | g/l | 27.8 | 0.1 | 28 | 2 | 47.4 |
| Glucose utilization | (1 − (g/l final/g/l initial)) × 100 | 100 | 0 | 100 | 0 | 100 |
| Galactose utilization | (1 − (g/l final/g/l initial)) × 100 | 100 | 0 | 100 | 0 | 78 |
| Mannose utilization | (1 − (g/l final/g/l initial)) × 100 | 100 | 0 | 100 | 0 | 97 |
| Ethanol yield: fermentable sugars | (g/l Ethanol/(0.51 × g/l initial fermentable sugar)) × 100 | 90.9 | 0.33 | 92 | 6.5 | 90 |
| Ethanol yield: total sugars | (g/l Ethanol/(0.51 × g/l initial total sugar)) × 100 | 90.9 | 0.33 | 91 | 6.5 | 90 |
| Ethanol metabolic yield | (g/l Ethanol/(0.51 × g/l sugars consumed)) × 100 | 90.9 | 0.33 | 91 | 6.5 | 91 |
| Volumetric Ethanol production rate | Maximum g/l Ethanol/total time hrs | 0.87 g/L/h | 0.00 | 0.70 g/L/h | 0.05 | 0.95 g/L/h |
| Cell yield | g Dry cell mass/g total consumed sugars | 0.07 g/g | 0.03 | 0.05 g/g | 0.01 | 0.03 g/g |

*Theoretical ethanol calculated as 0.51 g/g of sugar eliminated through sporulation and backcrossing to result in a homozygous diploid version of AG3.

Diploidization of yeast is routine in the art. See, for example, the Laboratory Course Manual that accompanys *Methods in Yeast Genetics,* 1986, Sherman et al., Cold Spring Harbor Laboratory, Cold Spring Harbor, N.Y.; Farahnak et al., 1986, *Appl. Environ. Microbiol.,* 51(2):362-367; Curran & Carter, 1983, *J. Gen. Microbiol.,* 129(5):1589-91; and Curran & Carter, 1986, *Curr. Genet.,* 10(12):943-5.

Example 6

Over-Expression of LPP1 in Yeast

The plasmid, pRS169-LPP1, was constructed by inserting the LPP1 gene behind the GAL1 promoter in the backbone vector, pRS169. D603 cells were then transformed with pRS169-LPP1 as well as pRS169, the control. Both strains grew in medium without the presence of uracil, and the D603/pRS169-LPP1 strain over-expressed LPP1.

Figure 17:
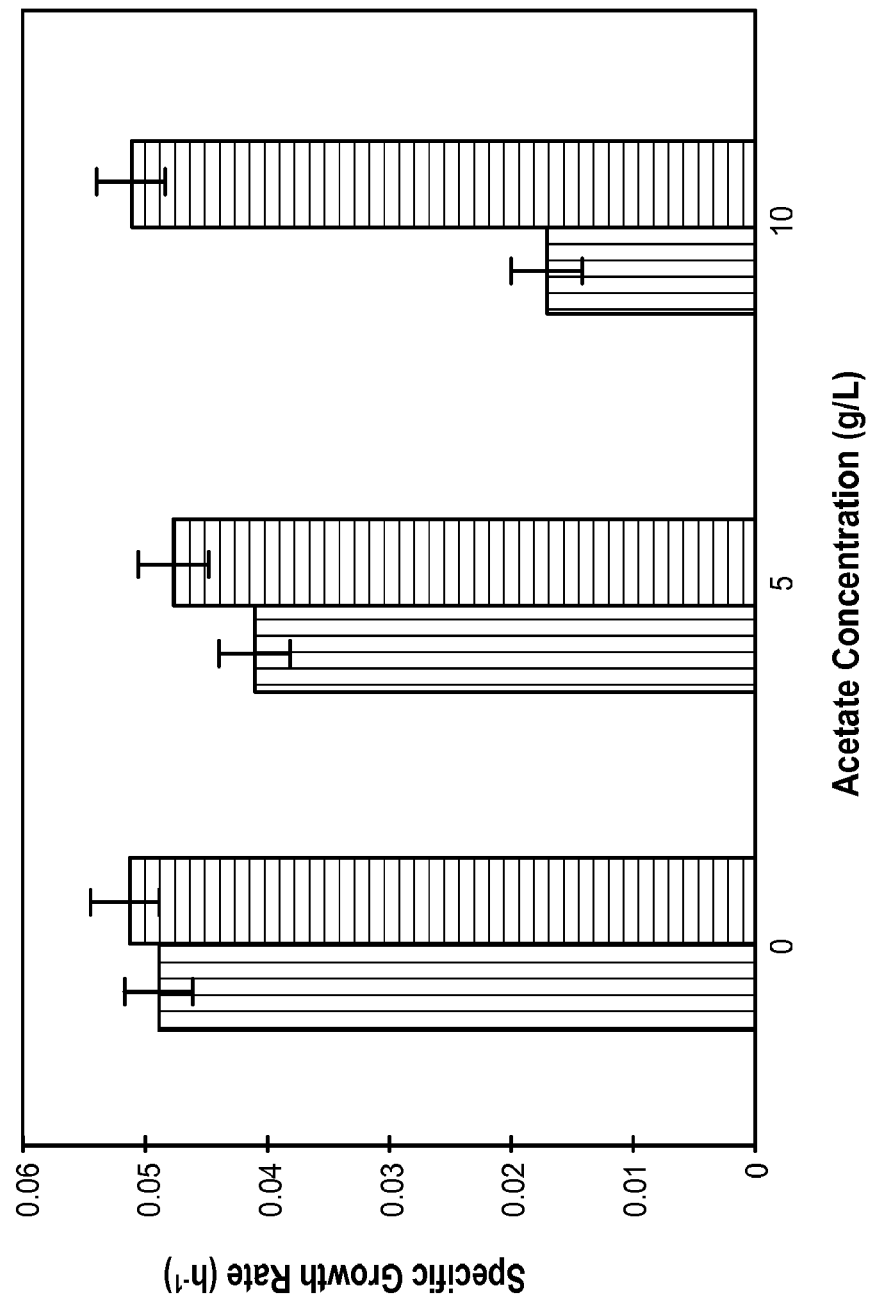
FIG. 17 is a graph showing the growth of the D603/pRS169 strain (light shading) and the D603/pRS169-LPP1 strain (dark shading).

Cells were cultivated on 20 g/L galactose with 6.7 g/L yeast nitrogen base without amino acids, 100 mg/L methionine, 100 mg/L adenine, 80 mg/L histidine, and 150 mg/L lysine. Uracil was omitted from the medium as selective pressure. Growth studies were performed at 30° C. with shaking. Sodium acetate trihydrate was added such that the total acetate present equals the specified concentration and the pH of the medium was adjusted to 5.6 using 40% (v/v) phosphoric acid. The results are shown in FIG. 17. These experiments demonstrated that over-expression of LPP1 confers acetate tolerance to *Saccharomyces cerevisiae*.

Example 7

Additional Yeast Mutants, AG4 and AG5

Cytostat experiments as described in Example 1 were used to produce the mutant *S. cerevisiae* strains, AG4 and AG5, disclosed herein. The feed medium was initially set to 20 g/L acetate. The cell number concentration was maintained at 450,000 cells/ml. At approximately 96 h, there was an increase in the cell number concentration, automatically couple with an increasing dilution rate. By 120 h, AG4 and AG5 were isolated from the bioreactor effluent stream. Through comparative genome hybridization using cDNA microarrays, it was determined that mutant strains AG4 and AG5 had an amplified Ena1, Ena2 and Ena5 gene as compared to the wild type s288c strain.

The AG3 strain was crossed with the AG5 strain using conventional methods, and the AG4 strain was crossed with the AG5 strain. The fermentation performances of the three *S. cerevisiae* strains, AG3, AG4 and AG5, and the crosses between those strains are summarized in Table 6. For these experiments, all the fermentations were performed using 100 g/L glucose, 20 g/L acetate, and 6.7 g/L yeast nitrogen base at pH 5.6 and 30° C. All yields were calculated as the maximum product secreted divided by the total glucose consumed.

TABLE 6

| | Wild type S288C | Mutant isolate AG3 | Mutant isolate AG4 | Mutant isolate AG5 | Mutant isolate cross AG3 × AG5 | Mutant isolate cross AG4 × AG5 | Industrial diploid strain Ethanol Red |
|---|---|---|---|---|---|---|---|
| Specific growth rate: 30° C., SD medium ($h^{-1}$) | 0.40 ± 0.00 | 0.40 ± 0.01 | 0.38 ± 0.01 | 0.36 ± 0.00 | 0.38 ± 0.01 | 0.41 ± 0.01 | 0.43 ± 0.03 |
| Growth rate: 30° C., 50 g/L EtOH, SD medium ($h^{-1}$) | 0.03 ± 0.01 | 0.08 ± 0.01 | 0.08 ± 0.01 | 0.09 ± 0.00 | 0.08 ± 0.00 | 0.10 ± 0.01 | |
| Growth rate: 30° C., 20 g/L acetate, SD medium ($h^{-1}$) | 0.15 ± 0.00 | 0.26 ± 0.01 | 0.26 ± 0.01 | 0.25 ± 0.02 | 0.25 ± 0.00 | 0.33 ± 0.02 | 0.13 ± 0.00 |
| Growth rate: 37° C., SD medium ($h^{-1}$) | 0.29 ± 0.02 | 0.37 ± 0.02 | 0.40 ± 0.01 | 0.35 ± 0.00 | 0.35 ± 0.01 | 0.38 ± 0.00 | |
| Ethanol Yield (g ethanol/g glucose) | 0.317 | 0.372 | 0.407 | 0.391 | 0.386 | 0.403 | 0.351 |
| Side product: acetate yield (g acetate/g glucose) | 0.014 | 0.009 | 0.008 | 0.009 | 0.007 | 0.008 | 0.005 |
| Side product: glycerol yield (g glycerol/g glucose) | 0.061 | 0.051 | 0.041 | 0.038 | 0.034 | 0.038 | 0.063 |
| Time required for ethanol production (h) | 120.92 | 70.75 | 61.50 | 63.75 | 63.83 | 54.33 | 68.83 |
| Mating type | α | α | α | a | α/a | α/a | |

The mutant strains isolated and constructed herein have improved specific growth rates with respect to the wild type yeast in the presence of high concentrations of acetate and ethanol as well as elevated temperatures. The progeny of the cross between AG4 and AG5 exhibit the highest tolerance to high acetate concentrations (20 g/L acetate) and produces ethanol at the highest rate of the strains tested.

Example 8

Furfural Tolerant Strains

AG5F and AG5F2 are derivatives of AG5, and have increased furfural tolerance in addition to the acetate tolerance. Strain AG5 was cultivated for approximately 17 h in 50 ml of SD medium (20 g/L glucose, 6.7 g/L Difco Yeast Nitrogen Base w/o Amino Acids) supplemented with 50 µg/ml hydrogen peroxide at 30° C. in a 250 ml Erlenmeyer flask with shaking at 250 rpm. Hydrogen peroxide has been shown to induce interchromosomal and intrachromosomal mutations. The cell number concentration was maintained at 450,000 cells/ml using SD medium supplemented with 0.5 g/L furfural. From separate isolation experiments, AG5F and AG5F2 were isolated by 120 h.

Figure 18:
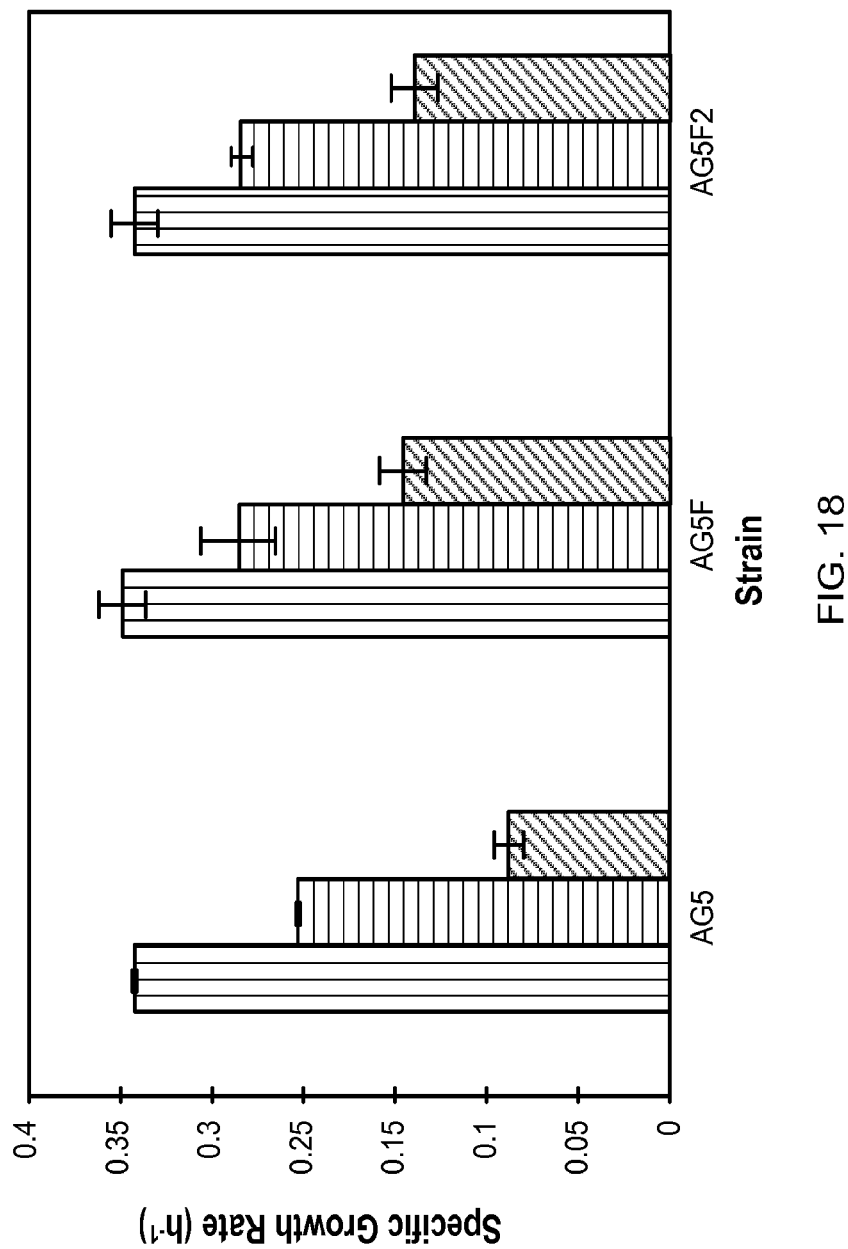
FIG. 18 is a graph showing the growth rates of AG5, AG5F, and AG5F2, determined from triplicate measurements at 30° C. Growth rates were determined on minimal medium (left columns), minimal medium supplemented with 20 g/L acetate (center columns), and minimal medium supplemented with 0.5 g/L furfural (right columns).

AG5F and AG5F2 have a growth advantage of 70% and 60%, respectively, over the parental strain in the presence of 0.5 g/L furfural, using a cell number concentration of less than 500,000 cells/ml. The AG5F and AG5F2 strains retain the high specific growth rate in minimal medium and in the presence of 20 g/L acetate. The results are summarized in FIG. 18.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. An *E. coli* bacterium, wherein said bacterium has been genetically-engineered to exhibit reduced, relative to wild type *E. coli*, or undetectable amounts of functional PPP1, OPM4r, ANA2, FEM3, TCA10, FEM2 and FEM7 polypeptides.

2. The bacterium of claim 1, wherein said bacterium utilizes 5-carbon and 6-carbon sugars simultaneously or essentially simultaneously in the production of ethanol.

3. The bacterium of claim 1, wherein said bacterium exhibits reduced or undetectable amounts of one or more of said functional polypeptides due to a mutation in a gene encoding said one or more polypeptides.

4. The bacterium of claim 1, wherein said bacterium exhibits reduced or undetectable amounts of one or more of said functional polypeptides due to deletion of a gene encoding said one or more polypeptides.

5. The bacterium of claim 1, wherein said bacterium comprises a deletion of each of the zwf, ndh, sfcA/maeB, ldhA, frdA, poxB and pta genes, wherein said deletion results in reduced or undetectable amounts of functional PPP1, OPM4r, ANA2, FEM3, TCA10, FEM2 and FEM7 polypeptides, respectively.

6. The bacterium of claim 1, wherein said bacterium produces ethanol at an increased rate compared to wild type *E. coli*.

7. The bacterium of claim 1, wherein said bacterium converts 5-carbon sugars to ethanol at a yield of at least 91% and up to at least 98%.

8. The bacterium of claim 1, wherein said bacterium converts a mixture of 5-carbon and 6-carbon sugars to ethanol at a yield of at least 85% and up to at least 95%.

9. The bacterium of claim 1, wherein, under appropriate fermentation conditions, said bacterium utilizes glycerol as a substrate in the production of ethanol.

10. The bacterium of claim 1, wherein said appropriate fermentation conditions include anaerobic conditions and the presence of an electron acceptor.

11. The bacterium of claim 10, wherein said electron acceptor is a nitrate.

12. The bacterium of claim 1, wherein said bacterium further exhibits reduced, relative to wild type *E. coli*, or undetectable amounts of functional MDH polypeptides.

13. An *E. coli* bacterium, wherein said bacterium has been genetically-engineered to exhibit reduced, relative to wild type *E. coli*, or undetectable amounts of functional PPP1, OPM4r, ANA2, FEM3, TCA10, FEM2, FEM7, GG1, GLK and MAN1 polypeptides.

14. The bacterium of claim 13, wherein said bacterium utilizes 5-carbon sugars exclusively or essentially exclusively in the production of ethanol.

15. The bacterium of claim 13, wherein said bacterium exhibits reduced or undetactable amounts of one or more of said functional polypeptides due to a mutation in a gene encoding said one or more polypeptides.

16. The bacterium of claim 13, wherein said bacterium exhibits reduced or undetectable amounts of one or more of said functional polypeptides due to a deletion of a gene encoding said one or more polypeptides.

17. The bacterium of claim 13, wherein said bacterium comprises a mutation in each of the zwf, ndh, sfcA/maeB, ldhA, frdA, poxB, pta, ptsG, glk and manX genes, wherein said mutation results in reduced or undetectable amounts of functional PPP1, OPM4r, ANA2, FEM3, TCA10, FEM2, FEM7, GG1, GLK and MAN1 polypeptides, respectively.

18. The bacterium of claim 13, wherein said bacterium produces ethanol at an increased rate compared to wild type *E. coli*.

19. The bacterium of claim 13, wherein said bacterium converts 5-carbon sugars to ethanol at a yield of at least 90%.

20. The bacterium of claim 19, wherein said conversion of 5-carbon sugars to ethanol is in the presence of 6-carbon sugars.

21. The bacterium of claim 13, wherein said bacterium further comprises at least one additional disruption that results in a bacterium that exhibits tolerance to higher concentrations of ethanol and/or acetate than does the bacterium of claim 13 or a bacterium that exhibits a faster rate of growth than does the bacterium of claim 13.

22. A method of making ethanol, comprising:
   contacting one or more sugars, under appropriate fermentation conditions, with the bacterium of claim 1, or the bacterium of claim 13.

23. The method of claim 22, further comprising collecting said ethanol.

24. The method of claim 22, wherein said one or more sugars are contacted with a) said bacterium of claim 1 or said bacterium of claim 13 and b) a *S. cerevisiae* yeast comprising at least a duplication of at least a portion of the lpp1 gene, or a *S. cerevisiae* yeast comprising at least a duplication of at least a portion of the ENA.

25. The method of claim 24, wherein said one or more sugars are contacted with a) and b) sequentially.

26. A method of converting lignocellulosic biomass into ethanol, comprising:
   hydrolyzing said lignocellulosic biomass to produce a hydrolysate comprising at least one sugar, and
   contacting at least one sugar from said hydrolysate, under appropriate fermentation conditions, with the bacterium of claim 1, or the bacterium of claim 13.

27. A method of converting glycerol to ethanol, comprising:
   contacting said glycerol with the bacterium of claim 1 under appropriate fermentation conditions.

28. The method of claim 27, further comprising collecting said ethanol.

* * * * *

UNITED STATES PATENT AND TRADEMARK OFFICE
CERTIFICATE OF CORRECTION

PATENT NO. : 8,623,622 B2  Page 1 of 1
APPLICATION NO. : 12/668982
DATED : January 7, 2014
INVENTOR(S) : Friedrich Srienc et al.

It is certified that error appears in the above-identified patent and that said Letters Patent is hereby corrected as shown below:

In the Specification

Column 1, Line 4, please insert the following paragraph after the title

-- STATEMENT AS TO FEDERALLY-SPONSORED RESEARCH

This invention was made with government support under R01-GM077529 awarded by the National Institutes of Health. The government has certain rights in the invention. --

In the Claims

Column 35, Line 63 (approx.), Claim 15, please delete "undectable" and insert -- undetectable --, therefor.

Signed and Sealed this
Seventeenth Day of June, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,623,622 B2 | Page 1 of 1 |
| APPLICATION NO. | : 12/668982 | |
| DATED | : January 7, 2014 | |
| INVENTOR(S) | : Srienc et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 345 days.

Signed and Sealed this
Fifth Day of May, 2015

Michelle K. Lee
*Director of the United States Patent and Trademark Office*

SEQUENCE LISTING

<160> NUMBER OF SEQ ID NOS: 24

<210> SEQ ID NO 1
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 1
cgcgtaacaa ttgtgg                                                    16

<210> SEQ ID NO 2
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 2
ctggattttt tccagc                                                    16

<210> SEQ ID NO 3
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 3
gcgttcaaaa ccctcggg                                                  18

<210> SEQ ID NO 4
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 4
gacaccaatc ccgatacccg cc                                             22

```
<210> SEQ ID NO 5
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 5
cggatgatgt tctgcatagc aggtg                                        25

<210> SEQ ID NO 6
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 6
cccaaccggc agaaaacgcc ccgct                                        25

<210> SEQ ID NO 7
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 7
ctgtttgatg ccgtctaact cgttc                                        25

<210> SEQ ID NO 8
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 8
ctttatccat gagtcgccgc ctgtg                                        25

<210> SEQ ID NO 9
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 9
cggtaattaa taaggcgcag agcg                                         24

<210> SEQ ID NO 10
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 10
ctccagtttt tgacaagggc                                              20

<210> SEQ ID NO 11
<211> LENGTH: 18
<212> TYPE: DNA
<213> ORGANISM: Artificial Sequence
<220> FEATURE:
<223> OTHER INFORMATION: synthetic oligonucleotide
```

```
<400> SEQUENCE: 11
cgcaacaaac gcggctac                                                 18

<210> SEQ ID NO 12
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 12
cggctttata tttacccagc                                               20

<210> SEQ ID NO 13
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 13
ctgccgctat gttgaagaca                                               20

<210> SEQ ID NO 14
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 14
gttcgcctgc ttcgttagtc                                               20

<210> SEQ ID NO 15
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 15
atggatatcg tcgggtttga                                               20

<210> SEQ ID NO 16
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 16
aagcaataac gttccggttg                                               20

<210> SEQ ID NO 17
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 17
ggatcggtta ctggtggaaa                                               20
```

```
<210> SEQ ID NO 18
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 18
gaccaccacg ttagccatct                                                 20

<210> SEQ ID NO 19
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 19
caggcacata aggcaatcag                                                 20

<210> SEQ ID NO 20
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 20
tattccttat gcggggtcag                                                 20

<210> SEQ ID NO 21
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 21
gcaaacgaat gtgacaagga                                                 20

<210> SEQ ID NO 22
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 22
cggttttcat atccccaaga                                                 20

<210> SEQ ID NO 23
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 23
ctggagacga tggatcaggt                                                 20

<210> SEQ ID NO 24
<211> LENGTH: 20
<212> TYPE: DNA
<213> ORGANISM: Artificial Sequence
```

```
<220> FEATURE:
<223> OTHER INFORMATION: synthetic oligonucleotide

<400> SEQUENCE: 24
caccacctgt tggaatgttg                                                   20
```